United States Patent
Sako et al.

(10) Patent No.: US 6,714,623 B2
(45) Date of Patent: *Mar. 30, 2004

(54) IMAGE COLLECTING SYSTEM

(75) Inventors: Tsukasa Sako, Utsunomiya (JP); Osamu Tsujii, Utsunomiya (JP)

(73) Assignee: Canon Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/553,958

(22) Filed: Apr. 21, 2000

(65) Prior Publication Data

US 2002/0159567 A1 Oct. 31, 2002

Related U.S. Application Data

(63) Continuation-in-part of application No. 09/385,048, filed on Aug. 30, 1999, now abandoned.

(30) Foreign Application Priority Data

| Aug. 31, 1998 | (JP) | 10-260902 |
| Apr. 27, 1999 | (JP) | 11-119620 |
| Aug. 24, 1999 | (JP) | 11-237190 |
| Aug. 27, 1999 | (JP) | 11-241751 |

(51) Int. Cl.$^7$ .............................................. H05G 1/56
(52) U.S. Cl. ........................ 378/98.8; 378/91; 378/115; 378/116
(58) Field of Search .................. 378/98.8, 4, 91, 378/98, 114, 115, 116

(56) References Cited

U.S. PATENT DOCUMENTS

| 5,337,341 | A | * | 8/1994 | Shimizu ...................... 378/98.2 |
| 5,541,656 | A | * | 7/1996 | Kare et al. ............. 348/333.02 |
| 5,773,832 | A | * | 6/1998 | Sayed et al. ........... 250/370.09 |
| 5,867,561 | A | * | 2/1999 | Strasser et al. ............ 378/98.2 |
| 6,084,939 | A | * | 7/2000 | Tamura ...................... 378/98.2 |
| 6,266,387 | B1 | * | 7/2001 | Gscheidmeier et al. ........ 378/4 |

* cited by examiner

Primary Examiner—Edward J. Glick
Assistant Examiner—Hoon Song
(74) Attorney, Agent, or Firm—Fitzpatrick, Cella, Harper & Scinto

(57) ABSTRACT

In an image collecting system for sensing an X-ray image by using a solid state image pickup unit, the operability of the system is improved by omitting an operation of turning on and off the solid state image pickup unit or other operations. When an operator selects an image sensing part of an object by using an acquisition part setting button on a display unit, the solid state image pickup unit is driven and a timer starts, and in addition, the sensing condition, image processing parameters and the like are automatically set in accordance with the selected sensing part. When an exposure button is depressed before the timer counts up, e.g., in 10 minutes, an X-ray generation control unit makes an X-ray tube radiate an X-ray to the object, and the solid state image pickup unit senses an X-ray image. If the exposure button is not depressed in 10 minutes, the operation of the solid state image pickup unit is stopped and the set sensing part is released.

17 Claims, 34 Drawing Sheets

FIG. 8

| CONTENTS OF PROCESSING | SETTING FORMULA | DEFAULT VALUE | LIVE REDUCED IMAGE PROCESSING PARAMETER | LIVE IMAGE PROCESSING PARAMETER |
|---|---|---|---|---|
| RADIATION FIELD RECOGNITION | AUTO | AUTO | AUTO | EQUAL TO DECIDED VALUE |
|  | SPECIFY | X, Y, W, H | COORDINATE SYSTEM OF 1/8 TIMES DEFAULT VALUE X/8, Y/8, W/8, H/8 | COORDINATE SYSTEM OF 1/8 TIMES DECIDED VALUE |
| IMAGE EMPHASIS | 0 (ORDINARY) 10 (LOW) 20 (MIDDLE) 30 (HIGH) | N | 1/2 TIMES DEFAULT N | TWICE DECIDED VALUE |
| GRADATION CONVERSION | AUTO | AUTO | AUTO | EQUAL TO DECIDED VALUE |

NOTE: LIVE IMAGE IS 2688×2688×12 BITS, LIVE REDUCED IMAGE IS 336×336×12 BITS

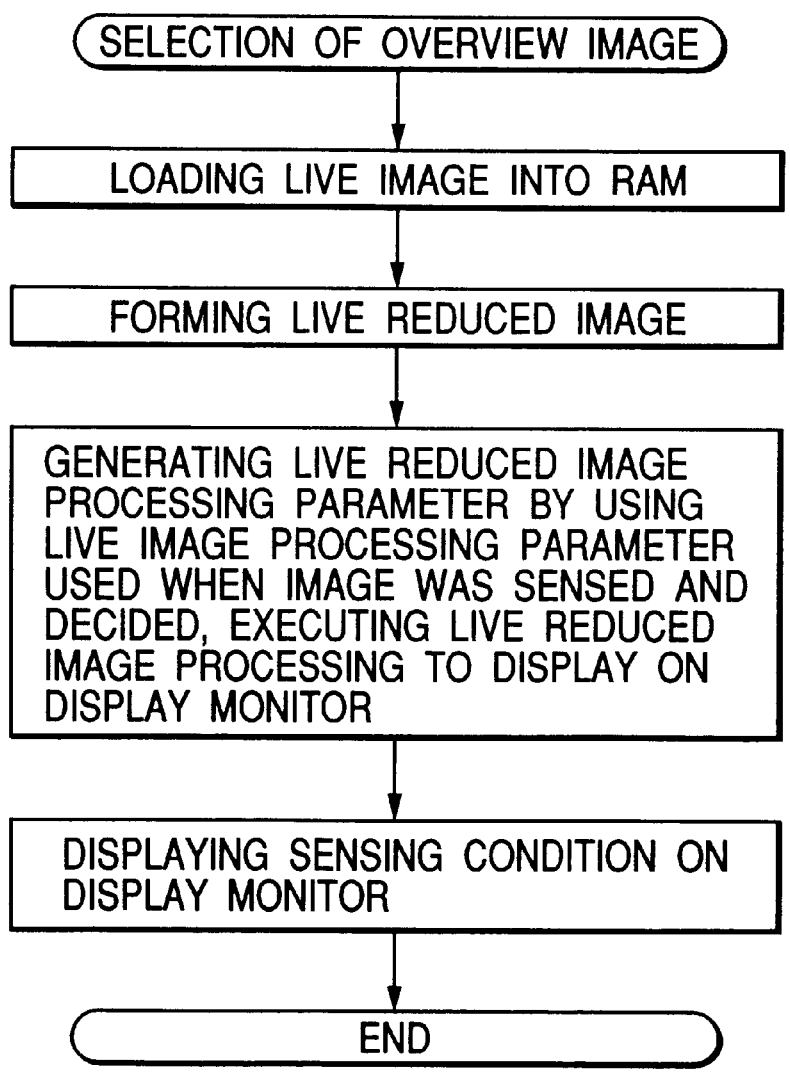

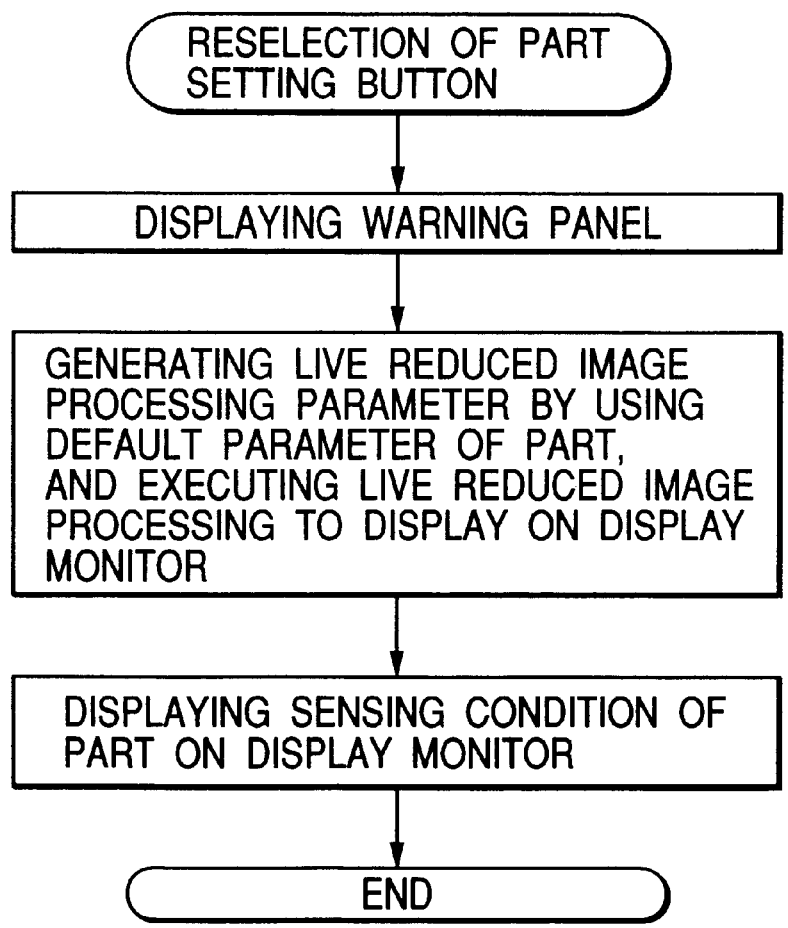

FIG. 11

| | |
|---|---|
| EXAMINATION ATTRIBUTION | PATIENT ATTRIBUTION<br>CHARACTERISTIC ATTRIBUTION OF EXAMINATION<br>NUMBER OF SENSED IMAGE |
| IMAGE ATTRIBUTION OF FIRST IMAGE | NAME OF PART<br>SENSING CONDITION<br>LIVE IMAGE PROCESSING CONDITION<br>IRREVERSIBLE COMPRESSION COEFFICIENT<br>IRREVERSIBLE COMPRESSION RATE<br>LIVE IMAGE FILE NAME |
| IMAGE ATTRIBUTION OF SECOND IMAGE | THE SAME AS ABOVE |
| | ⋮ |
| IMAGE ATTRIBUTION OF N-th IMAGE | THE SAME AS ABOVE |

FIG. 12

| QID | IMAGE PROCESSING | TRANSFER 1 | TRANSFER 2 | TRANSFER 3 | TRANSFER 4 | ERASE | EXAMINATION FILE NAME |
|---|---|---|---|---|---|---|---|
| 2329 | DONE | DONE | DONE | DONE | ON EXECUTING (TID=1) | UNDONE | F02329.QUE |
| 2330 | ON EXECUTING (TID=2) | UNDONE | UNDONE | UNDONE | UNDONE | UNDONE | F02330.QUE |
| 2331 | UNDONE | UNDONE | UNDONE | UNDONE | UNDONE | UNDONE | F02331.QUE |
| 2332 | UNDONE | UNDONE | UNDONE | UNDONE | UNDONE | UNDONE | F02332.QUE |
| 2333 | UNDONE | UNDONE | UNDONE | UNDONE | UNDONE | UNDONE | F02333.QUE |
| 2334 | UNDONE | UNDONE | UNDONE | UNDONE | UNDONE | UNDONE | F02334.QUE |

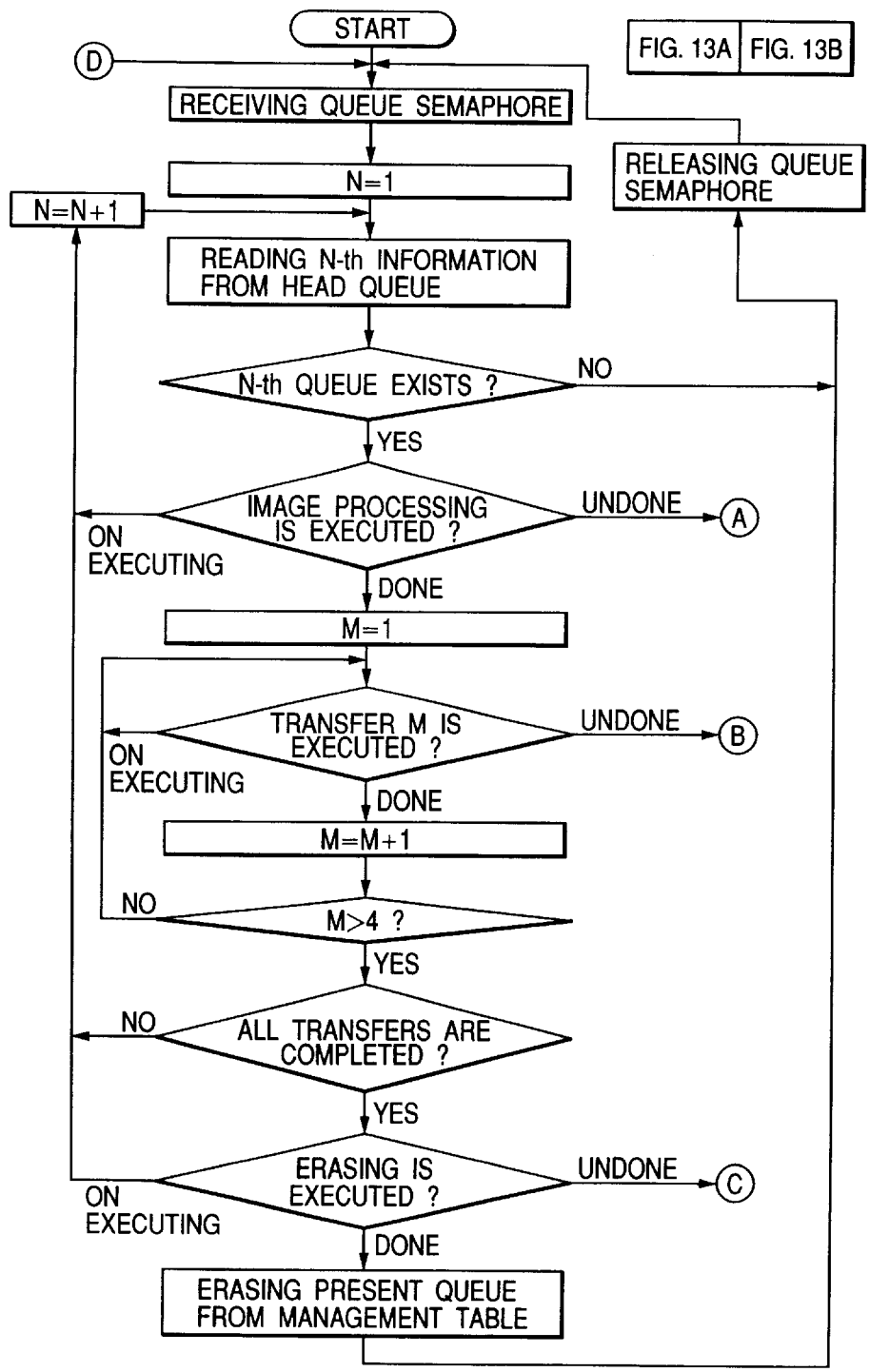

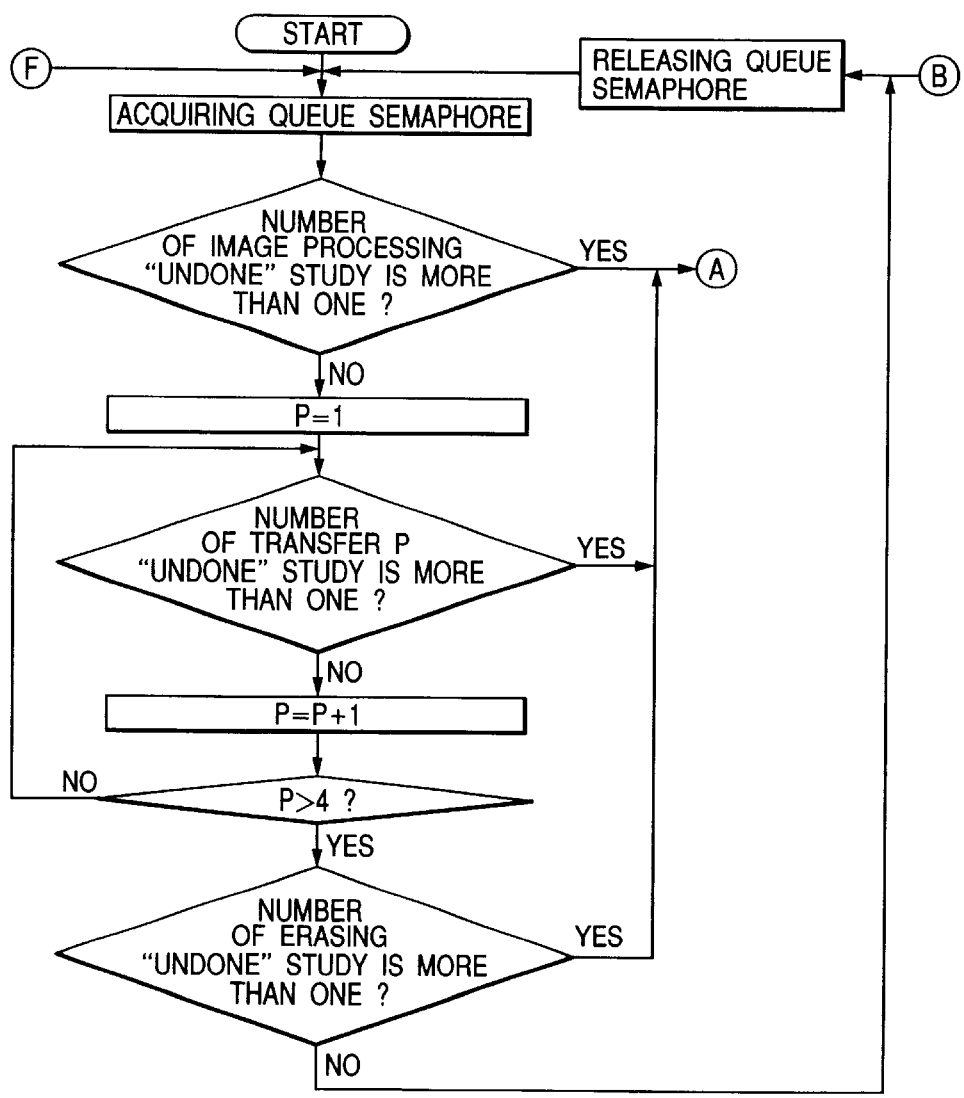

IMAGE COLLECTING SYSTEM

This is a continuation-in-part application of U.S. patent application Ser. No. 09/385,048 filed on Aug. 30, 1999, now abandoned.

BACKGROUND OF THE INVENTION

1. Field of the Invention

The present invention relates to an X-ray image collecting system and method for collecting X-ray images and to a computer readable storage medium storing programs realizing the X-ray image collecting method.

2. Related Background Art

In the medical field, an image sensed by X-ray and developed on a film is used for medical diagnosis, by placing the X-ray film on a film viewer. A general X-ray film has a contrast in a density range from about 1.0 to 1.5 D so as to facilitate to diagnose an examination part of a human body. If the sensing conditions are shifted more or less, the film becomes under-exposure or over-exposure and diagnosis becomes difficult. If an examination part is to be sensed divisionally, since each divided part has a different contrast and a different examination objective, the sensing conditions are required to be minutely controlled.

With the recent development of computer technologies, computers are prevailing also in the medical field. This trend is fast also in the image diagnosis field. There is a rapid progress in various CTs, ultrasonic diagnosis equipments, radio isotope diagnosis equipments and the like. A concept "collective image diagnosis" has come into existence. This concept means a collective diagnosis of images of various modalities to be performed by interconnecting various diagnosis equipments by computers. X-ray film images are most often used in image diagnosis and considered as important. However, since the X-ray film image is essentially an analog image, it is difficult to process it in the collective image diagnosis by using computers.

X-ray image sensing by using solid state image pickup elements has been developed recently. Reading a sensed x-ray digital image by using computers is now gradually performed in practice. If an X-ray digital image sensing apparatus is used, the contrast of an image once sensed can be adjusted thereafter or the image failed to be senced can be sensed immediately thereafter.

The X-ray digital image sensing apparatus is, however, associated with some problem. Namely, an X-ray technical person is required to enter various sensing conditions via a computer. If the technical person is not accustomed with computers or medical equipments, it is difficult to properly operate these computers or medical equipments.

In the case of an image collecting system using solid state image pickup elements, it is necessary to drive the image pickup elements before an image is sensed. The image pickup elements are not stable in operation immediately after they are driven. It takes a delay time of several seconds or several tens seconds to stably sense an image. In order to sense an image at any time, it is required to always maintain the image pickup elements in a drive state. It is well known, however, that if they are always maintained active, the life time of them is shortened. In order to avoid this, an operator is required to activate the image pickup elements each time when an image is to be sensed, and to wait until the delay time lapses, being unable to sense the image immediately. The operator therefore feels cumbersome.

SUMMARY OF THE INVENTION

It is an object of the present invention to provide an image collecting system capable of making an operator easily operate the system without considering the sensing conditions.

It is another object of the invention to provide image pickup means capable of sensing an image of X-ray passed through an object without any wasteful drive time and prolonging the life time of the image pickup means.

In order to achieve the above objects, according to one aspect of the invention, there is provided an image collecting system comprising: information inputting means for inputting information necessary for image sensing; and control means for making image sensing means for sensing an object image enter a drive state, in accordance with an output of the information inputting means.

Another aspect of the invention provides an image collecting system comprising: X-ray generating means for exposing an object to an X-ray; image sensing means for sensing an image of an X-ray transmitted through the object; information inputting means for inputting information necessary for image sensing; exposure permitting means for permitting the X-ray generating means to expose the object to the X-ray; and control means for making the image sensing means for sensing an object image enter a drive state, in accordance with an output of the information inputting means, and making the image sensing means enter a non-drive state if the exposure permitting means does not permit exposure of the X-ray in a predetermined time after the information is input to the information inputting means.

Another aspect of the invention provides an image collecting system comprising: information inputting means for inputting information necessary for image sensing; receiving means for receiving a request from the information inputting means; and control means for making image sensing means for sensing an object image enter a non-drive state, if the receiving means does not receive the request.

Another aspect of the invention provides an X-ray image collecting system comprising: X-ray generating means for exposing an object to an X-ray; image sensing means for sensing an image of an X-ray transmitted through the object, the image sensing means including a solid state image pickup unit; setting means for setting an image sensing part of the object; exposure instructing means for instructing the X-ray generating means to expose the object to the X-ray; and control means for making the image sensing means enter a drive state in accordance with setting by the setting means, and making the image sensing means enter a non-drive state if the exposure instructing means does not instruct to expose the object to the X-ray in a predetermined time after the setting.

Another aspect of the invention provides an image collecting method comprising the steps of: inputting information necessary for image sensing; and making image sensing means for sensing an object image enter a drive state, in response to an input of the information.

Another aspect of the invention provides an image collecting method comprising the steps of: inputting information necessary for image sensing to information inputting means; receiving a request from the information inputting means at receiving means; and making image sensing means for sensing an object image enter a non-drive state, if the receiving means does not receive the request.

Another aspect of the invention provides an X-ray image collecting method comprising the steps of: setting an image sensing part of an object; making image sensing means including a solid state image pickup unit enter a drive state after the setting step; instructing to expose the object to an X-ray after the image sensing means enters the drive state; sensing an image of an X-ray transmitted through the object with the image sensing means; and making the image sensing means enter a non-drive state if there is no instruction to expose the object to the X-ray in a predetermined time after the setting step.

Another aspect of the invention provides a computer readable storage medium storing a program, the program comprising the steps of: detecting an input of information necessary for image sensing; and making image sensing means for sensing an object image enter a drive state in response to a detection of the information.

Another aspect of the invention provides a computer readable storage medium storing a program, the program comprising the steps of: receiving information necessary for image sensing; and making image sensing means for sensing an object image enter a non-drive state if the information necessary for image sensing is not received.

Still another aspect of the invention provides a computer readable storage medium storing a program, the program comprising the steps of: setting an image sensing part of an object; making image sensing means including a solid state image pickup unit enter a drive state after the setting step; instructing to expose the object to an X-ray after the image sensing means enters the drive state; sensing an image of an X-ray transmitted through the object with the image sensing means; and making the image sensing means enter a non-drive state if there is no instruction to expose the object the X-ray in a predetermined time after the setting step.

The other objects and features of the invention will become more apparent from the following detailed description of embodiments when read in conjunction with the accompanying drawings.

BRIEF DESCRIPTION OF THE DRAWINGS

FIG. 8 is a diagram showing the structures of image processing default values, live reduced image processing parameters and live image processing parameters.

FIG. 9 is a flow chart illustrating an operation of selecting an overview image.

FIG. 10 is a flow chart illustrating an operation of reselecting a part setting button.

FIG. 11 is a diagram showing the format of an examination file.

FIG. 12 is a diagram showing the structure of a queue table.

DETAILED DESCRIPTION OF THE PREFERRED EMBODIMENTS

First, a solid state image pickup unit for picking up an image of X-ray transmitted through an object will be described, this unit being used with the first, second and third embodiments to be later described.

Figure 1:
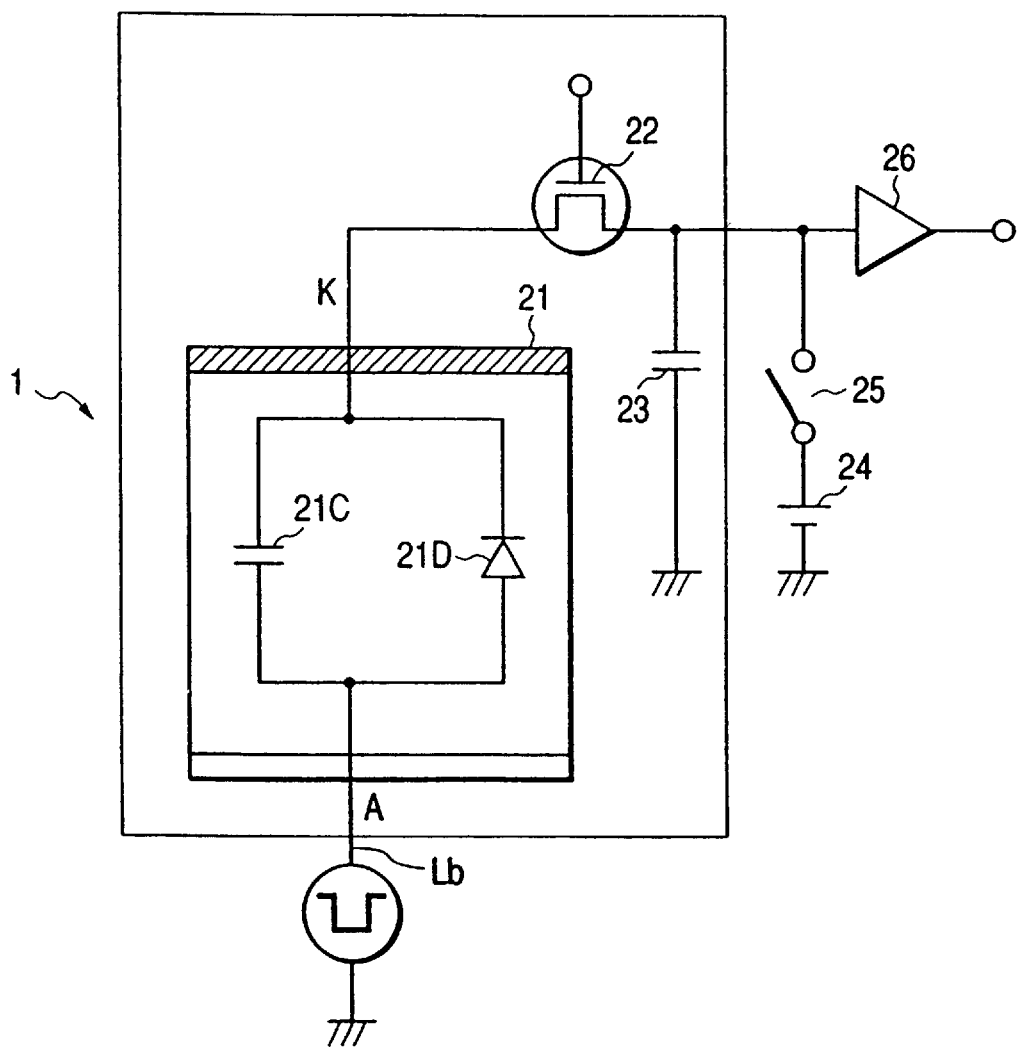
FIG. 1 is a schematic diagram showing one pixel of a conventional solid state image pickup unit.

FIG. 1 is an equivalent circuit of one pixel constituting a solid state image pickup unit. In the following description, the solid state image pickup unit is assumed to be a two-dimensional amorphous silicon sensor. However, the sensor is not necessarily limited to the two-dimensional amorphous silicon sensor, but various other sensors may be used, such as a charge coupled element and a photo multiplier tube. Referring to FIG. 1, one pixel includes a photodetector unit 21 and a switching TFT 22 for controlling charge accumulation and charge read, respectively. Generally, each pixel is made of amorphous silicon (α-Si) deposited on a glass substrate. Alphanumeric symbol 21C in the photodetector unit 21 represents either a parasitic capacitance of a photodiode 21D or a capacitor 21C for improving the dynamic range of the photodetector unit 21D. The anode A of the diode 21D is connected to a bias wiring line Lb which is a common electrode, and the cathode K thereof is connected to the switching TFT 22 capable of controlling to read charges stored in the capacitor 21C. In this example, the switching TFT 22 is a thin film transistor connected between the cathode K of the diode 21D and a charge read amplifier 26.

After the capacitor 21C is reset by using the switching TFT 22 and a reset switching element 25, an X-ray beam 1 is radiated so that the photodiode 21D generates charges corresponding to the radiation amount of the beam and the capacitor 21C stores the charges. Thereafter, the switching TFT 22 and reset switching element 25 are operated again to transfer the charges to a capacitor element 23. The transferred charges are read as a potential signal by a pre-amplifier 26 and A/D converted to thereby detect the amount of incidence radiation.

Figure 2:
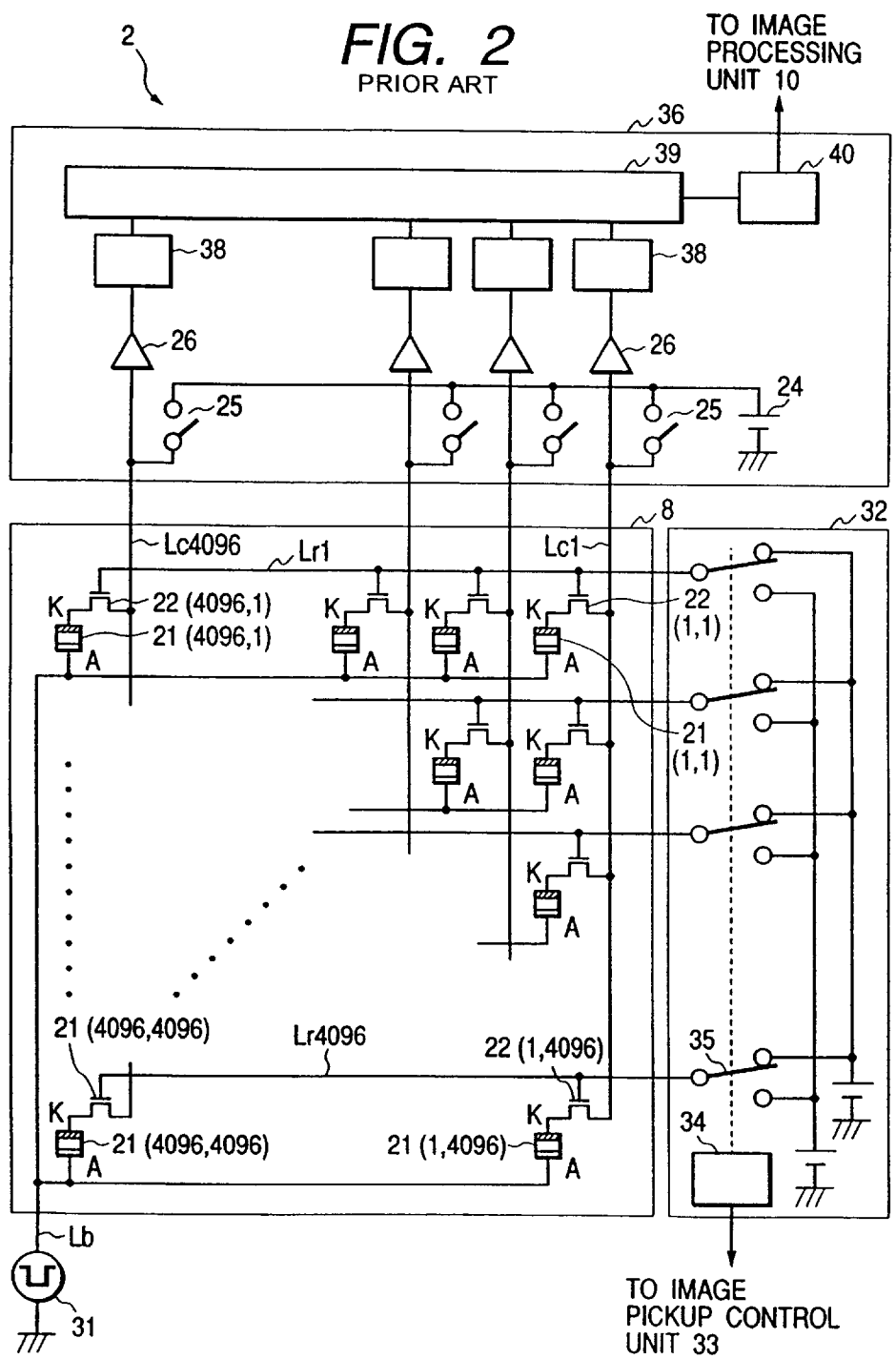
FIG. 2 is a schematic diagram showing a conventional solid state image pickup unit.

FIG. 2 is an equivalent circuit of the solid state image pickup unit 2 two-dimensionally disposed. Using pixels shown in FIG. 1 being two-dimensionally disposed, photoelectric conversion operation of the solid state image pickup unit will be described.

The solid state image pickup unit has pixels of about 2000×2000 to 4000×4000, and an array area of about 200 mm×200 mm to 500 mm×500 mm. In the example shown in FIG. 2, a photosensor array 8 is comprised of 4096×4096 pixels and has an array area of 430 mm×430 mm. The size of one pixel is therefore about 105 $\mu$m×105 $\mu$m. Pixels are disposed two-dimensionally by disposing 4096 pixels horizontally in one block and 4096 pixels vertically.

In the example shown in FIG. 2, the photodetector array 8 having 4096×4096 pixels is formed on a single substrate. However, the photodetector array 8 having 4096×4096 pixels may be made of four photodetector arrays each having 2048×2048 pixels. In this case, some merit such as an improved manufacture yield can be obtained.

As described previously, one pixel is constituted of the photoelectric conversion element 21 and switching TFT 22. Reference numerals 21-(1, 1) to 21-(4096, 4096) correspond to the photoelectric conversion elements 21. The cathode of each photodetector diode is represented by K and the anode thereof is represented by A. Reference numerals 22-(1, 1) to 22-(4096, 4096) correspond to the switching TFTs 22.

The K electrode of the photoelectric conversion element 21-(m, n) of each column of the two-dimensional photodetector array 8 is connected to a column signal line (Lc1 to Lc4096) common to each column via the source-drain conductive path of the corresponding switching TFT 22-(m, n). For example, the photoelectric conversion elements 21-(1, 1) to 21-(1, 4096) of the first column are connected to a first column signal line Lc1. The electrode A of the photoelectric conversion element 21 of each row is connected to a bias power supply 31 for mode switching via a bias line Lb common to each row. The gate electrode of TFT 22 of each row is connected to a row select line (Lr1 to Lr4096). For example, TFTs 22-(1, 1) to 22-(4096, 1) of the first row are connected to a first row select line Lr1. The row select line Lr is connected to an image pickup control unit 33 via a line selector unit 32. For example, the line selector unit 32 is constituted of an address decoder 34 and 4096 switching elements 35. Using this structure, pixels in any desired line can be read. In the simplest way, the line selector unit 32 may be constituted of a shift register commonly used by a liquid crystal display.

The column signal line Lc is connected to a signal read unit 36 which is controlled by the image pickup control unit 33. Reference numeral 25 represents a switch for resetting the column signal line Lr to a reference potential of a reset reference power supply 24. Reference numeral 26 represents a pre-amplifier for amplifying a signal potential. Reference numeral 38 represents a sample/hold circuit, reference numeral 39 represents an analog multiplexer, and reference numeral 40 represents an A/D converter. A signal on each column signal line Lrn is amplified by the pre-amplifier 26 and held by the sample/hold circuit 38. An output of the sample/hold circuit 38 is sequentially supplied by the analog multiplexer 39 to the A/D converter 40 whereat it is converted into a digital signal and transferred to an image processing unit 10.

In the photodetector array 8, 4096×4096 pixels are allocated to 4096 lines Lcn, and outputs of 4096 pixels per one column are transferred at the same time via the column signal line Lc to the pre-amplifiers 26-1 to 26-4096, sample/hold circuits 38-1 to 38-4096 and to the analog multiplexer 39 which sequentially supplies the image signal to the A/D converter 40.

Although a single A/D converter 40 is shown in FIG. 2, it is usually constituted of 4 to 32 series which perform A/D conversion at the same time. This is because it is necessary to shorten an image signal read time without making the analog signal bandwidth and A/D conversion rate unnecessarily high. The details of the A/D converter will be later given.

A storage time is tightly related to an A/D conversion time. If high speed A/D conversion is performed, an analog circuit bandwidth becomes broad and a desired S/N ratio is difficult. It is requested that an image signal read time should be shortened without making the A/D conversion speed unnecessarily fast. In order to shorten the image signal read time, a number of A/D converters 40 are used for A/D conversion. However, in this case, the cost rises. The number of A/D convertors is therefore set to a proper value from the standpoint of cost.

The radiation time of a beam 1 is about 10 to 500 msec. It is proper to set a read time of one frame or a charge storage time to the order of 100 msec or shorter.

For example, in order to read an image in 100 msec by sequentially driving all the pixels at the analog signal bandwidth of about 50 MHz and at a sampling rate of 10 MHz, four series of A/D converters 40 at the minimum are necessary. In this image pickup apparatus, 16 series of A/D converters 40 are used to perform A/D conversion at the same time. Outputs of the 16 series of A/D converters 40 are stored in corresponding 16 series of unrepresented memories (such as FIFOs). These memories are selectively switched to obtain consecutive image data corresponding to one scan line and transfer the image data to the image processing unit 10 or its memory. Thereafter, the image data is displayed on a display unit as images or graphics.

Generally, the on-off cycle of a solid state image pickup unit is one time a day. For example, the power of the solid state image pickup unit is turned on when the operation test of the X-ray generator apparatus is performed. Thereafter, the power is maintained on during the period while there is a possibility that an object such as a patient is sensed. After images of that day have been completely sensed, the power is turned off.

It is rare that X-ray image sensing with the solid state image pickup unit is continuously performed during the power-on period. If the solid state image pickup unit is maintained on during the long time while no image sensing is preformed, a large consumption power is lost. Furthermore, in this embodiment, there is a phenomenon that the on-resistance of TFT 22 of an amorphous silicon device increases as the operation time is prolonged. This results in a lowered sensor sensitivity. From these reasons, the solid state image pickup unit is supposed to enter a standby state while no image sensing is performed, in order to suppress the consumption power and reduce the load of the image pickup unit by releasing it from the image sensing.

More specifically, all the drive lines Lc, Lr and Lb of the photodetector array 8 are set to the same potential, e.g., the ground potential. The other peripheral circuits such as selector unit 32, signal read unit 36 and image pickup control unit 33 are made to maintain their outputs or enter a state not causing any problem, to thus standby in a low current consumption mode. This mode is called a standby state (non-drive state).

When the standby state (non-drive state) changes to a normal image sensing state (drive state), the solid state image pickup unit prepares for sensing images. In this case, a predetermined wait time including the image sensing preparation time is required in order to obtain a good image quality and reproductivity. For example, this predetermined wait time may include a time necessary for the peripheral circuit elements such as the line selector unit 32 and signal read unit 26 to enter a steady state, a time necessary for the characteristics of the photodetector array 8 to become sufficiently stable in order to obtain a good image quality, and a time necessary for the dark current characteristics to become stable.

A first embodiment of the invention will be described with reference to the accompanying drawings.

Figure 3:
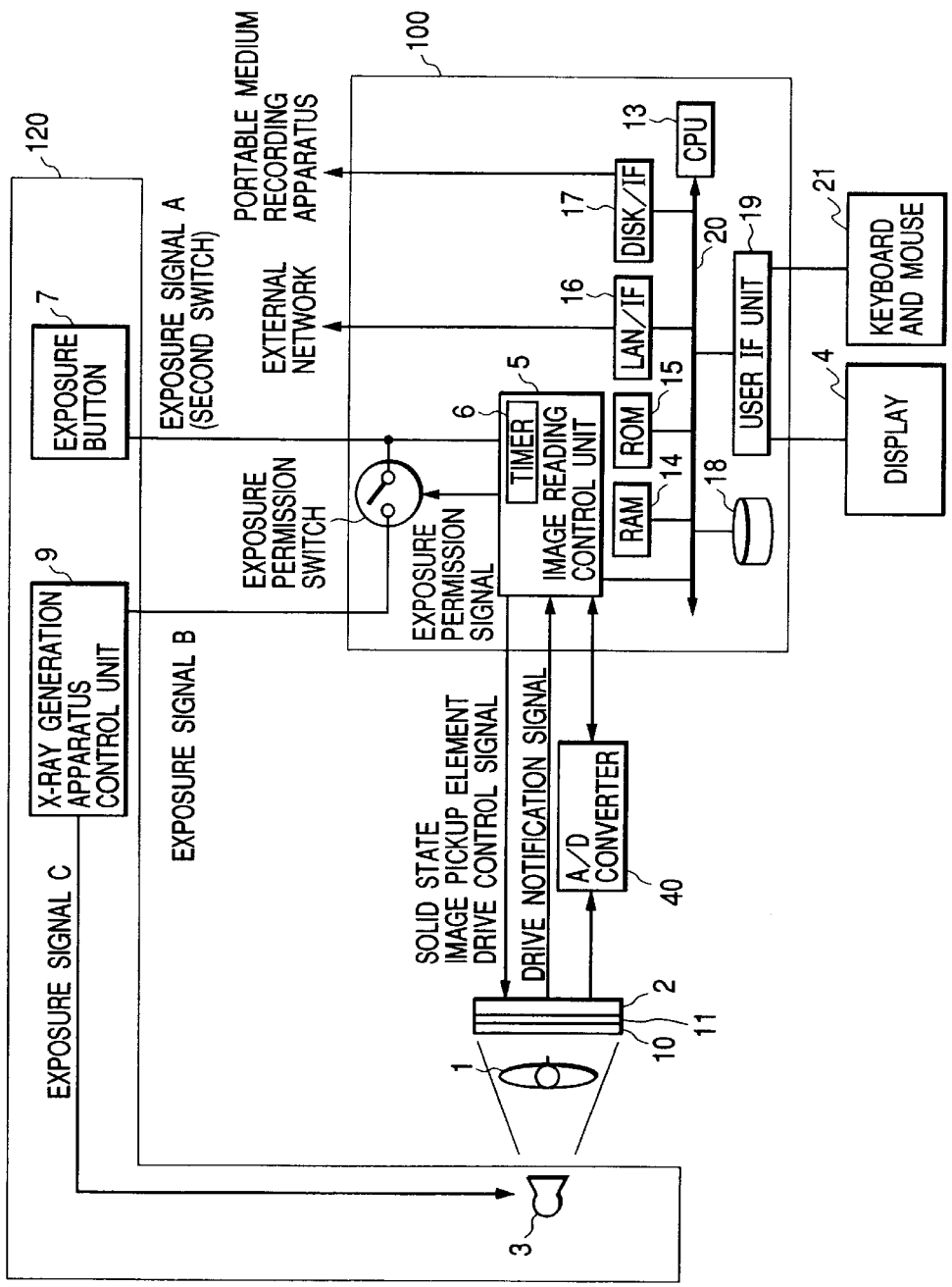
FIG. 3 is a diagram showing the structure of an X-ray image collecting system according to first to third embodiments of the invention.

FIG. 3 shows the structure of an X-ray image collection system according to the first embodiment of the invention.

An operator guides an object between the solid state image pickup unit 2 described above and an X-ray tube 3. Next, in order to set a sensing part, the operator depresses a part setting button displayed on a display unit 4. In response to this operation, an image reading control unit 5 of an image reading apparatus 100 generates a solid state image pickup unit drive control signal to apply voltage to the solid state image pickup unit 2 for the preparation of image sensing by the unit 2 at any time, and starts an internal timer 6.

Next, when an exposure button 7 is depressed, an exposure signal A is input to the image reading control unit 5. In response to this, the image reading control unit 5 checks from a state of a drive notification signal supplied from the unit 2 whether the unit 2 can receive an X-ray beam and sense an image. If the state is satisfied, the image reading control unit 5 generates an exposure permission signal to turn on an exposure permission switch 8 so that the exposure signal A is supplies to an X-ray generation apparatus control unit 9 as an exposure signal B. After the X-ray exposure is prepared, the X-ray generation apparatus control unit 9 generates an exposure signal C when an X-ray beam is radiated from the X-ray tube 3. The exposure signal A is generated upon actuation of a switch called a second switch. The X-ray tube 3, X-ray generation apparatus control unit 9 and exposure button 7 constitute an X-ray generation apparatus 120.

An X-ray transmitted from an object 1 is input as an image to a solid state image pickup unit 2 via a grid 10 and a scintillator 11. This image is read and digitalized by an A/D converter 40, and then transferred to an image reading control unit 5. In this embodiment, the solid state image pickup unit 2 and A/D converter 40 are discrete components.

The image reading control unit 5 is managed by a CPU 13. CPU 13 is connected via a bus 13 to a RAM 14, a ROM 15, a LAN/IF 16, a DISK/IF 17, a non-volatile storage unit 18, a user IF unit 19 and the like. The user IF unit 19 is connected to a keyboard 4 and a mouse 21 to interface with a user. The non-volatile storage unit 18 may be a hard disk.

The image input to the image reading control unit 5 is temporarily stored in RAM 14 to be subjected various image processing by CPU 13.

Figure 5:
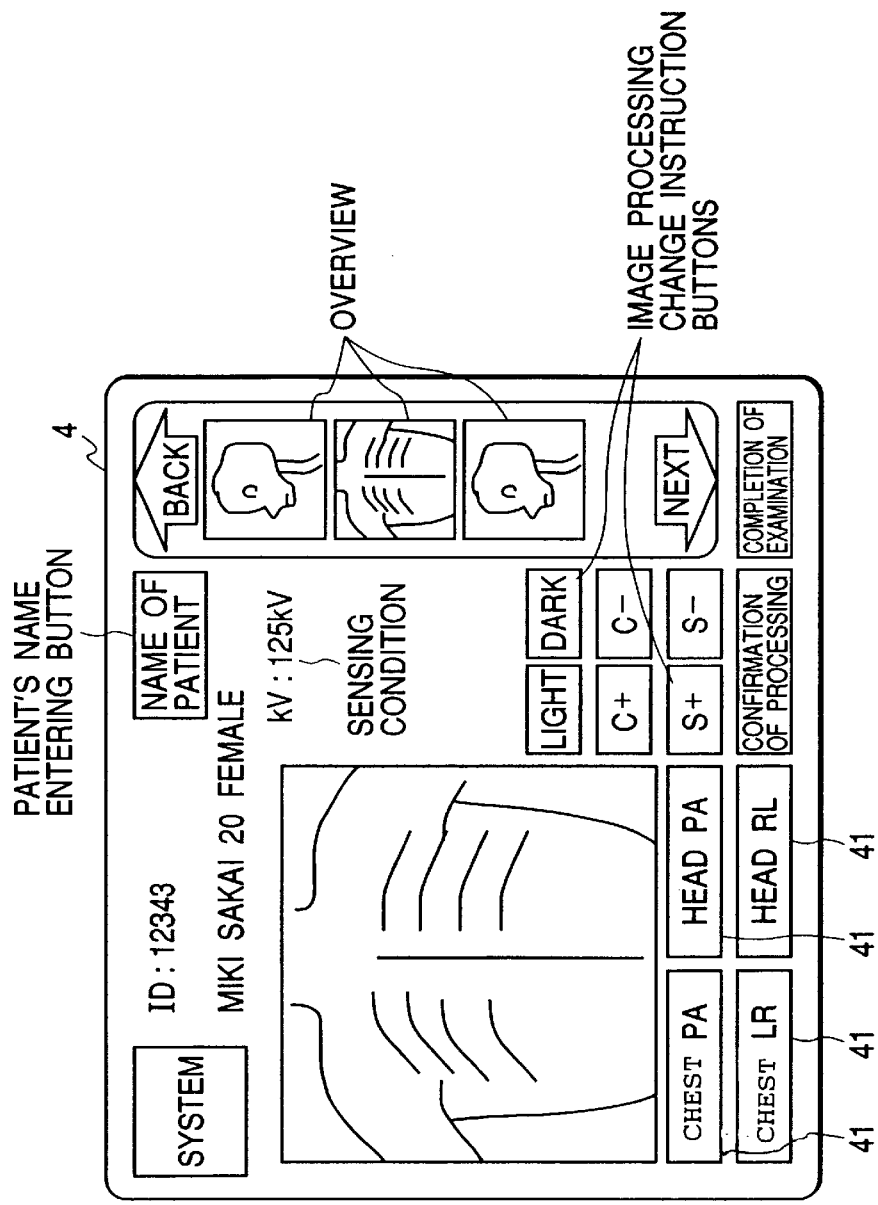
FIG. 5 is a diagram showing the structure of a display unit.

FIG. 5 shows an example of a displayed screen of the display unit 4.

When an image is to be sensed, an operator selects a part setting button 41. The part setting button 41 is initially in a non-selection state, and when it is depressed by the operator, it enters a selection state. If a part setting button not intended by an operator is erroneously depressed, the operator can depress again a correct part setting button.

The part setting button 41 is used not only for setting a part of the object to be sensed, but also for determining and managing a default value of image processing. In addition, when this part setting button is depressed, the solid state image pickup unit 2 is made active by the solid state image pickup unit drive control signal shown in FIG. 3, and a timer 6 in the image reading control unit 5 is made to start.

Figure 6:
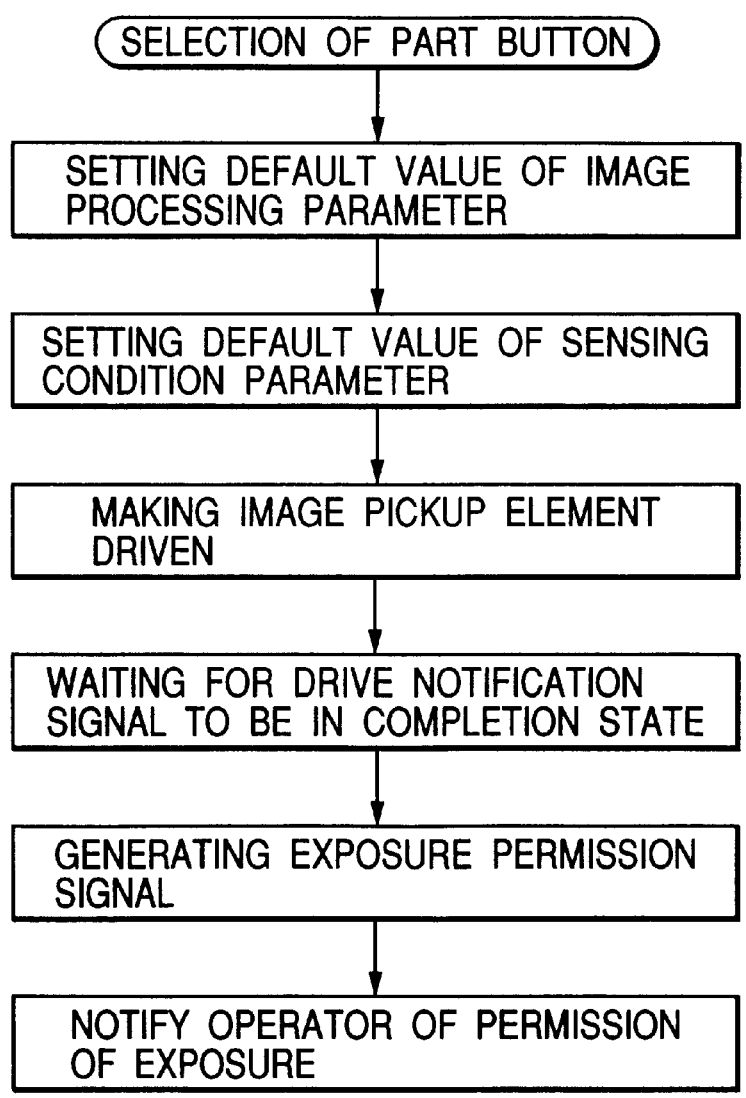
FIG. 6 is a flow chart illustrating an operation of selecting a part setting button.

FIG. 6 is a flow chart illustrating the operation of the X-ray image collecting system.

When the part setting button is selected and depressed, the solid state image pickup unit 2 is made active. After a delay time of several seconds to several tens seconds until a stable image can be output, the solid state image pickup unit 2 sends a drive notification signal to the image reading control unit 5. In response to this, the image reading control unit 5 outputs the exposure permission signal to turn on the exposure permission switch 8 to allow the second switch to be operated upon.

Figure 4:
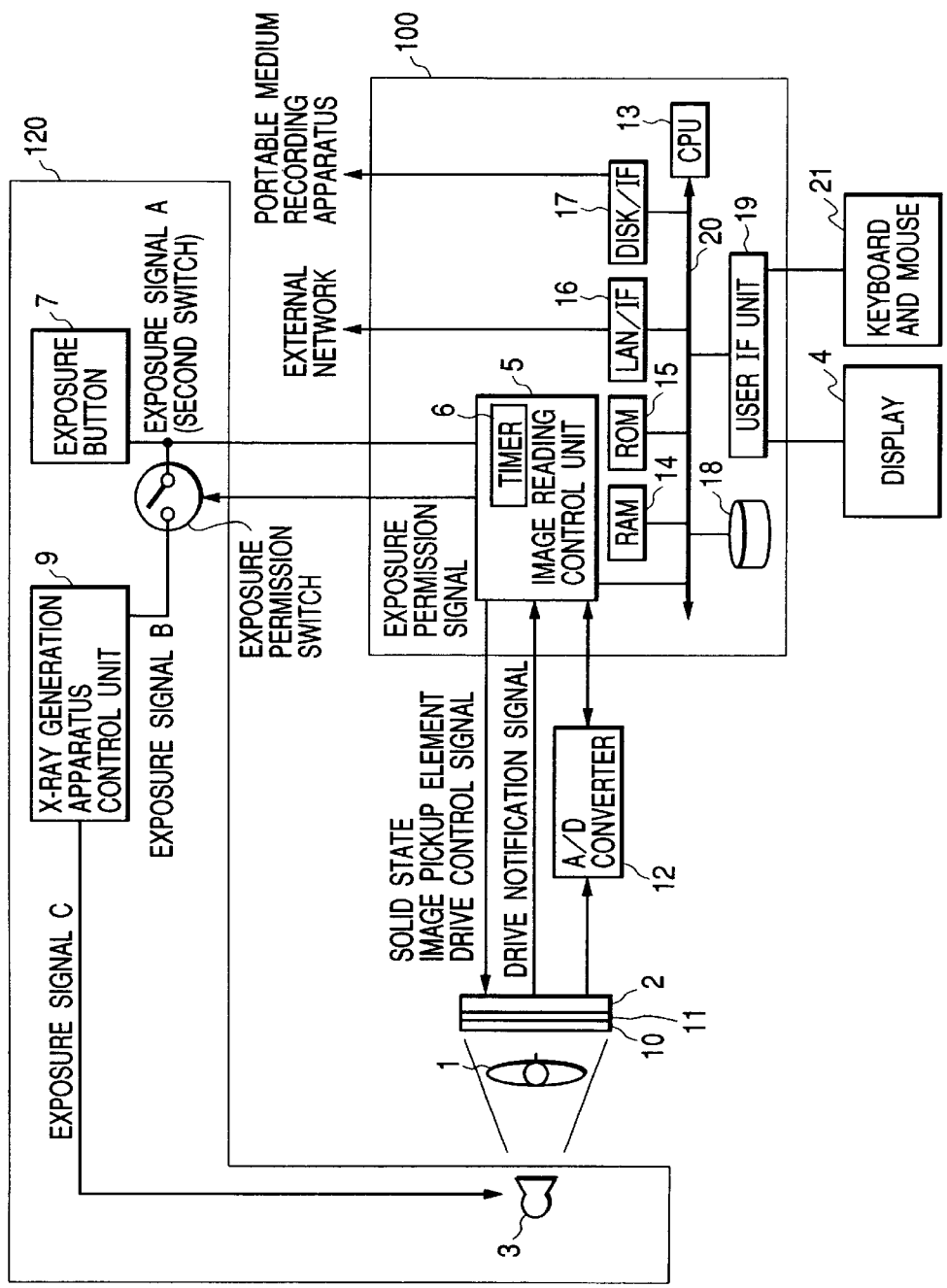
FIG. 4 is a diagram showing the structure of an X-ray image collecting system according to a modification of the first embodiment of the invention.

Depending upon the type of an X-ray generation apparatus, there is an X-ray generation apparatus having the exposure permission switch built therein, such as shown in FIG. 4. In this case, the image reading apparatus notifies the X-ray generation apparatus of the exposure permission signal. The image reading apparatus judges, from the exposure signal A supplies upon actuation of the exposure button, whether exposure was performed or not.

Thereafter, exposure permission is notified to the operator on the display unit 4 via the user interface unit 19. For example, this notice is performed by changing the background color on the screen of the display unit 4 from blue to green.

Next, the operation of the timer 6 will be described. Each time the operator depresses the part setting button, the timer 6 starts counting from 0, and after a predetermined time, e.g., after 10 minutes, this time is notified to the image reading control unit 5. The image reading control unit 5 releases the drive state of the solid state image pickup unit 2 (changes to the non-drive state), also suppresses the exposure permission signal to open the exposure permission switch 8, and notifies CPU 13 of a disabled state of the X-ray generation apparatus.

When the disabled state of the X-ray generation apparatus is notified, CPU 13 changes the selection state of the part setting button selected by the operator to a non-selection state, and notifies the operator of a disabled exposure on the display unit 4. For example, contrary to the above, the background color of the display unit 4 is changed from green to blue.

It is therefore possible to prevent the solid state image pickup unit 2 from being maintained always in the drive state and being deteriorated.

The operator is required to enter patient information such as a patient name. When a patient name entering button is clicked with the mouse, a patient information input window appears. By using the keyboard and mouse, the operator enters a patient name, a patient ID, a year-month-day of birth, an age and the like. This patient information may be entered before or after the part is selected, or after the images are collected if the X-ray image collecting system is not in the disabled state. In other words, the patient information can be entered at any time unless an examination end button is depressed to finish sensing a plurality of images of the patient. Even if there is no sufficient time for entering the patient information such as a patient name because of a critical condition of patient, image sensing can be executed first and thereafter the patient information can be entered.

In this system, there is a mode of selecting a sensing part always after the patient information is entered. In this case, at the timing when the patient information is entered, the solid state image pickup unit 2 is made active and the timer 6 is made to start. When the operator depresses thereafter the part setting button, the system immediately enters the exposure permission state because the solid state image pickup unit has already been activated. Also in such a case, if exposure is not performed, a time-out occurs and the solid state image pickup unit 2 is made inactive. If exposure is performed in this mode, the timer 6 is reset and immediately started again. Therefore, even if the part setting button is again depressed, images can be sequentially sensed without any delay time because the solid state image pickup unit has already been activated.

Figure 7:
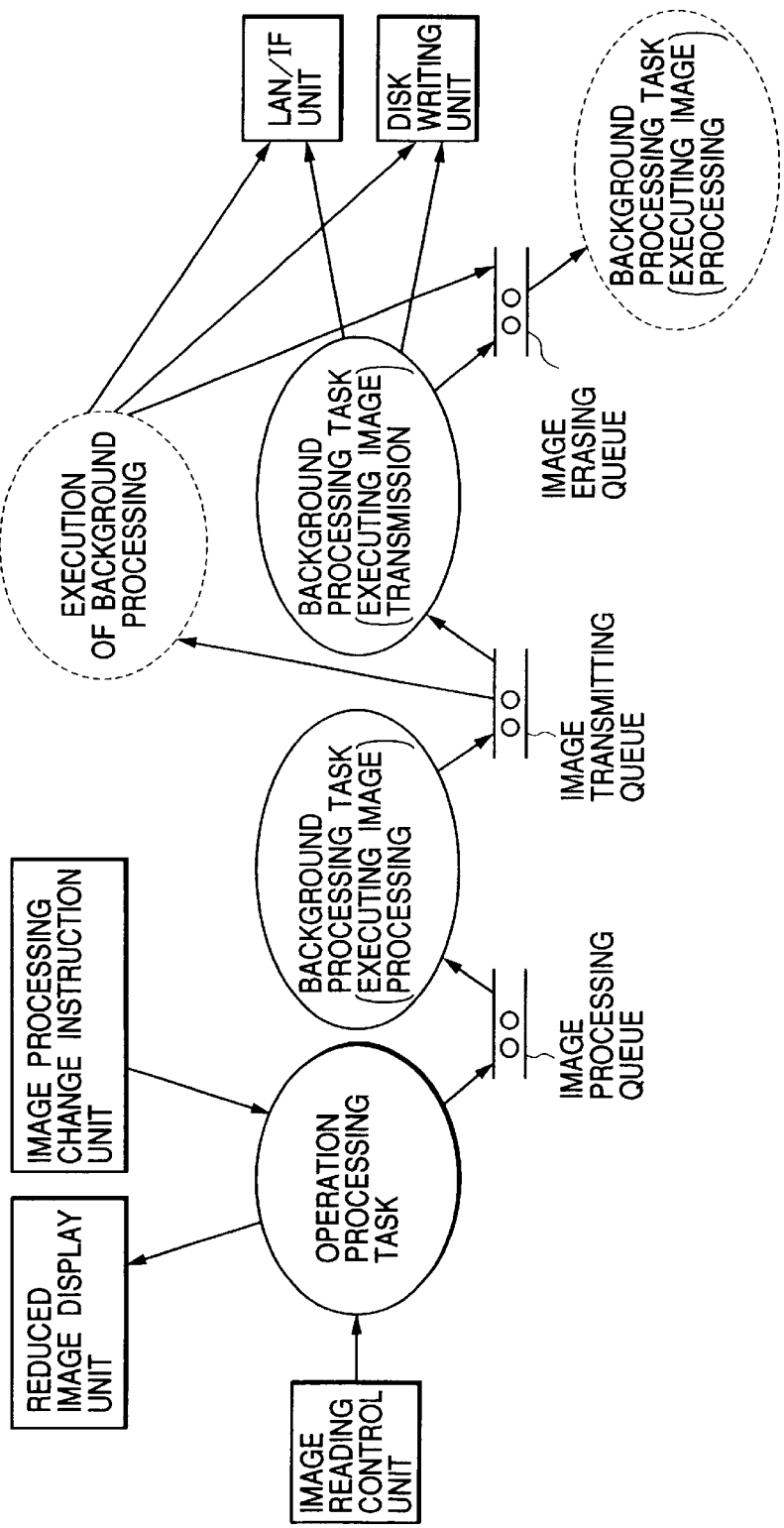
FIG. 7 is a diagram illustrating a task structure of an image reading apparatus.

FIG. 7 is a diagram showing the task structure of the image reading apparatus 100. The operation to be executed after images are collected will be described with reference to FIG. 7.

First, the task structure will be described. CPU 13 of the image reading apparatus 100 time divisionally performs a plurality of tasks. An operation processing task executes mainly a process activated by an operator manipulation. A background processing task executes collected image processing when necessary, transfers processed images to a network or to an external large capacity disk, and erases the images already transferred and copied. When images are to be transferred to the external device, images are irreversibly compressed by using predetermined irreversible compression coefficients, for example, by DCT of JPEG. The background task also executes this irreversible compression process.

In FIG. 7, although four tasks including broken line circles are shown, the feature of this system resides in that four or more works are performed by four tasks or less. In the example shown in FIG. 7, a plurality of four works or more are performed by two tasks so that two circles are shown by broken lines. The number of active tasks during image sensing is different from the number of active tasks not during image sensing. When the operator starts sensing, two tasks are activated. If the next image sensing is not performed after one minute lapse from the preceding image sensing, the number of active tasks increases to three. This time-out can be set from a setting panel.

When the image sensing starts, the number of active tasks is decreased to two. The task is not made inactive while it operates, but it is made inactive after its operation is completed. Since the number of active tasks reduces when the operator manipulation starts, it is possible to perform a background process without hindering the image sensing operation.

An image processing queue is provided between an operation processing task and an image processing task, this queue being a non-volatile FIFO system to be used for processing a sensed image. An image transmitting queue is provided between an image processing task and an image transferring task, this queue being a non-volatile FIFO system to be used for transferring an image processed by the image processing task. An image erasing queue is provided between an image transmitting task and an image erasing task, this queue being a non-volatile FIFO system to be used for erasing an image already transmitted and copied.

By using these FIFO systems, image processing and image transmitting tasks which take a relatively long time can be performed in parallel. The operation processing task which is required to have a high speed response can be performed smoothly. Even if the operation of the system is completed while the image processing and image transmitting tasks are performed, images will not be lost.

Reverting to FIG. 3, when the exposure button 7 is depressed by the operator before a lapse of a time determined by the timer 6, e.g., in 10 minutes after the part setting button was depressed, an image sensed with the solid state image pickup unit 2 is input via the A/D converter 40 to the image reading control unit 5. The image reading control unit 5 executes a correction process among those image processing which can be performed by hardware. Thereafter, the processed image is transferred from the image reading control unit 5 to RAM 14. This transfer is a DMA transfer between the image reading control unit 5 and RAM 14 without intervention of CPU 13. Therefore, the transfer can be performed at high speed. The image is a square image having horizontal 2688 pixels and vertical 2688 pixels, each pixel having a 12-bit gradation. This image is hereinafter called a live image.

The operation processing task reduces the size of collected images. This size reduced image is called hereinafter a live reduced image. This size is 336×336×12 bits. When the image is reduced, sampling is performed. Immediately thereafter, the operation processing task saves the live image in the non-volatile storage unit 18. Then, the operation processing task obtains live reduced image processing parameters from the default values preset for each part of the live reduced image, in accordance with a predetermined rule, and in accordance with the parameters, processes the image and displays it on the display unit.

In this embodiment, radiation field recognition, image emphasis and gradation conversion are performed in this order as the image processing. The image processing is performed always on the basis of 4096 tonal grey scale, and an image is lastly written in a display area of 336×336×8 bits and displayed on the display unit. In this case, since the user I/F unit 19 has a gamma correction table, the linearity of the display unit 4 can be corrected.

FIG. 8 shows the details of parameters for each type of image processing. The default values for the three types of image processing are preset for each part of the live reduced image and live image. The radiation recognition is a routine of extracting the radiation field area of an image which is used as density decision parameters when the gradation conversion is performed. The radiation field area is also used as cut information which is used for cutting only a necessary image portion to be transmitted to a network. If a setting formula of the radiation field recognition is automatic, the radiation field for the live reduced image is automatically recognized. Since the live reduced image has a size one eighth that of the live image, it is necessary to multiply the cut area width, height and cut start position by 8 when the live reduced image is processed.

It is also possible for an operator to specify a radiation field area by clicking with the mouse the upper left and lower right corners of the radiation field in the live reduced image displayed on the display unit. Also in this case, it is necessary to multiply the cut area width, height and cut start position by 8.

Without performing the radiation field recognition, a predetermined area may be designated. In this case, the cut area information is used as the default value which is divided by 8 to use it for the live reduced image.

The image emphasis is a frequency emphasis of an image. The parameter values are classified into four groups from 0 to 30 and the default values are preset for each sensing part. If the image emphasis process is performed for the live reduced image by using the default value, there is a tendency that the live reduced image is emphasized visually excessively as compared to the live image processed by using the same default value. If the image emphasis parameter divided by 8 is used because of the image size ratio of ⅛, the image emphasis cannot be recognized visually. It is empirically known that if the live reduced image is processed by using the parameters set for the live image and divided by 2, the live reduced image emphasis becomes visually equal to that of the live image.

The operator may change the image emphasis parameter by clicking "S+" or "S−" button shown in FIG. 5 with the mouse. The live reduced image processing parameters determined by the operator are required to be multiplied by 2 for the live image processing parameters.

The parameters for the gradation conversion can be decided automatically by using the radiation field area obtained by the radiation field recognition. The same parameters decided for the live reduced image are used also for the live image. As described earlier, the operation processing task obtains live reduced image processing parameters from the default values preset for each part of the live reduced image, in accordance with a predetermined rule. This rule is not always confined to a division by 8.

After the image processing is completed, a processing confirmation button shown in FIG. 5 is depressed. Then, the part setting button is selected with the mouse in order to sense the next image. If all the images for the patient have been sensed, an examination completion button is selected with the mouse. In response to the operator manipulation, the image reading control unit irreversibly compresses the display live reduced image of 336×336×8 bits by using the irreversible compression coefficients preset for each part of the image. The compression rate is calculated from a ratio of an original image byte size to a compressed image byte size. The irreversible compression coefficients are different for each part, for example, because a relatively fine image is required for a chest, whereas even a highly compressed image of a bone is sufficient for diagnosis by an orthopaedist. The calculated compression rate is stored together with image attributes to be later used.

As described above, images can be sequentially sensed for each patient. Before the examination completion button is depressed, it is necessary that the patient information has already been entered. If the patient information was not entered by using the patient name button, the patient name input window is automatically opened when the examination completion button is depressed, to thus urge the operator to enter the patient name from the patient name input window. After all the patient information is entered from the patient name input window and an input confirmation button is depressed, the examination is automatically terminated and a series of images sensed during this examination is input to the image processing queue as one queue.

In this embodiment, as shown in FIG. 5, the already sensed images are displayed as live reduced images on an overview screen. By selecting an overview image with the mouse, the already sensed image can be displayed again. Namely, the live image corresponding to the selected overview image stored in the non-volatile storage unit is again developed on RAM, and thereafter the operation processing task is performed similar to the normal sensing process.

FIG. 9 is a flow chart illustrating the operation to be executed when an operator selects an overview image. First, the live image is developed on RAM. Then, a live reduced image is formed. The live image processing parameters used by the operator when the image was sensed are used as the default values shown in FIG. 8 which are converted into the live reduced image processing parameters by using the rule illustrated in FIG. 8. In accordance with the converted live reduced image processing parameters, the live reduced image processing is performed to display again the live reduced image. Lastly, the sensing condition is displayed on the display unit.

The feature of this embodiment resides in that after the live image stored in the non-volatile storage unit is again developed on RAM, the part setting button is selected to use the sensed image as another part of the image. More specifically, even if an operator selected an erroneous part setting button and the image was sensed, this image can be later processed as a correct part by using corresponding correct attribute information.

FIG. 10 is a flow chart illustrating this part changing operation. After the already sensed image corresponding to the selected overview image is again displayed on the display unit and when the part setting button is depressed, an alarm notice of a part change is displayed. When the operator depresses a confirmation button, the live reduced image process is performed by using the live image processing default parameters for the selected part, and the processed live reduced image is displayed. The preset values for the selected part are also displayed as the sensing condition. In this case, it is obvious that the operator can change the image processing conditions, like during the normal sensing operation.

The examination completion button is selected in order to complete an examination for a single image or a plurality of images, as described earlier. In this case, as already described with reference to FIG. 7, all the post processes of the examination to be executed by this system are executed through a multi-task process on the background. Therefore, the operator can perform the next examination immediately thereafter.

FIG. 11 shows the format of an examination file formed when the examination is completed. Each time the examination completion button is selected, one examination file is formed. This examination file is constituted of one examination attribute and a plurality of image attributes. The examination attribute includes a patient attribute, an examination specific attribute, and the number of sensed images. The patient attribute includes a patient ID, a patient name, a year-month-day of birth, a gender and the like. The examination specific attribute includes an examination ID, an examination date, an examination time and the like. The number of sensed images corresponds to the total number of image attributes written in this examination file. The image attribute includes a part name, a sensing condition, a live image processing condition, an irreversible compression rate, and a live image file name.

The part name is the name of a sensed part. The sensing condition includes an X-ray tube voltage, current and the like. The live image processing condition includes the live image processing parameters shown in FIG. 8. The irreversible compression coefficient and rate have been described above. The live image file name is the name of a file of a live image stored in the non-volatile storage unit by the image reading control unit. This examination file contains all link information to the examination information and an image file. Therefore, the system of the embodiment can be configured by managing the examination files in a non-volatile queue.

Reverting to FIG. 7, the image processing, image transmitting and image erasing are performed on the background, while data is transferred to and from the image processing queue, image transmitting queue and image erasing queue. In this embodiment, these image processing queue, image transmitting queue and image erasing queue are managed by one table, which is one of the features of the embodiment. This table is hereinafter called a queue table.

FIG. 12 shows the details of the queue table. After the examination file of one examination with several images of one patient is stored in the non-volatile storage unit and entered in the image processing queue shown in FIG. 7, a new QID is issues and added to the last line of the queue table. This queue table is rewritten by a plurality of background processing tasks and a signal operation processing task. Therefore, an exclusive process called a semaphore process is performed to prevent a task from rewriting the queue table while another task rewrites the queue table. Acquisition of a right of rewriting the queue table is hereinafter called "acquire a semaphore", and inhibiting of this right is called "release a semaphore".

Figure 15:
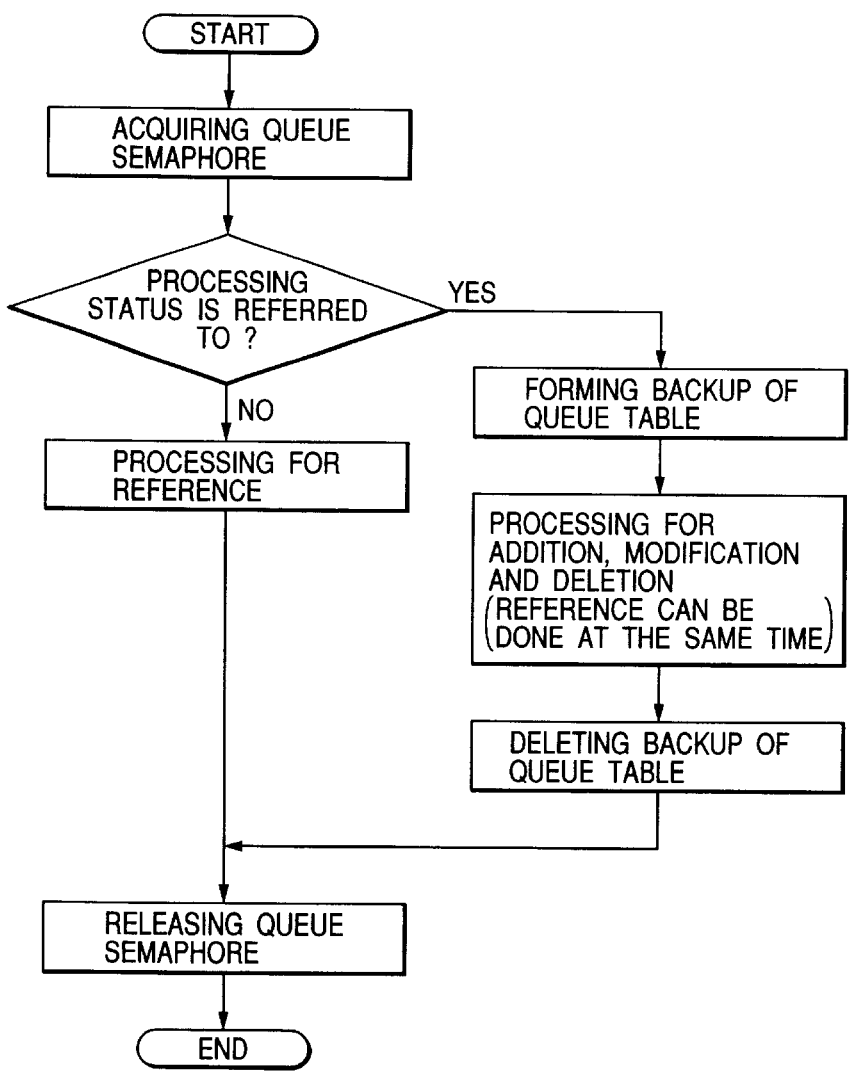
FIG. 15 is a flow chart illustrating an operation of reference, addition, correction and erasure relative to a queue table.
Figure 16:
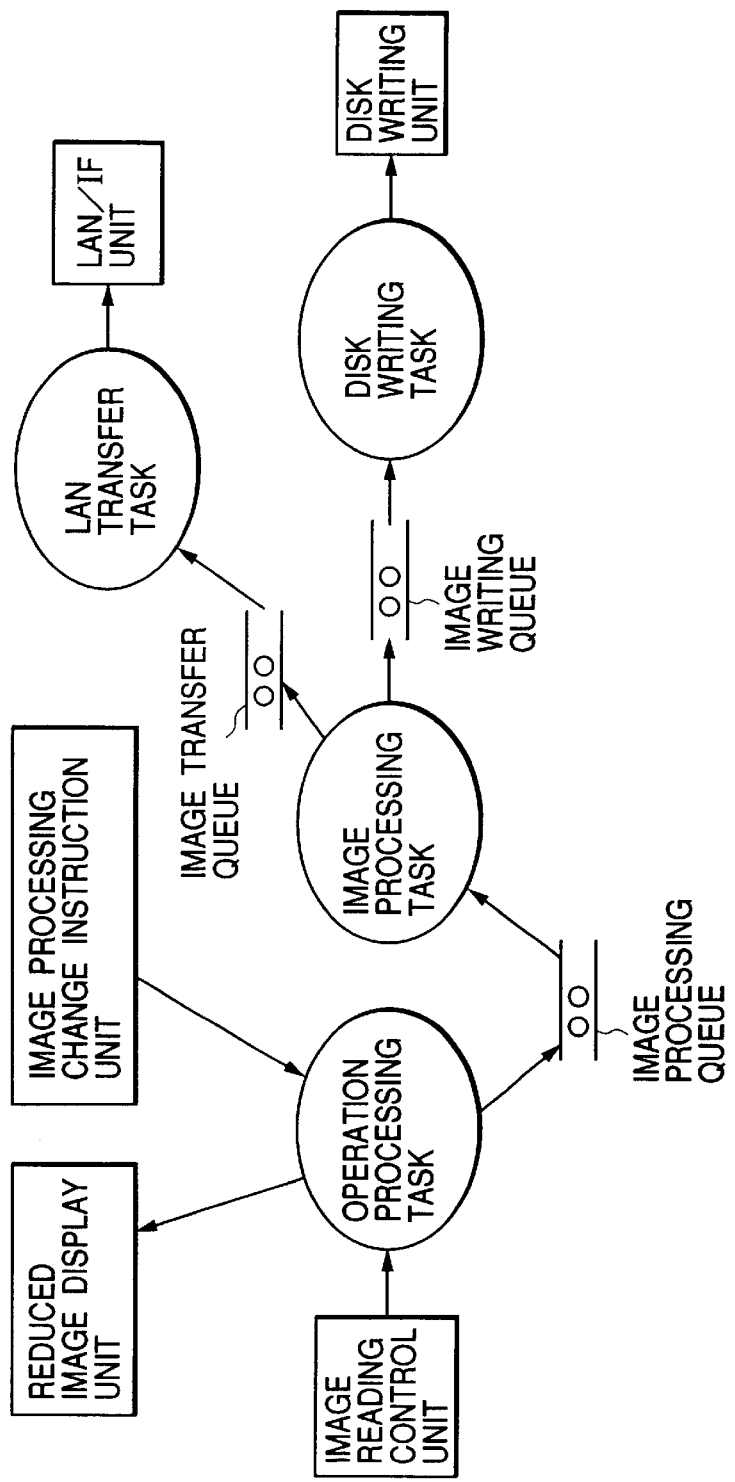
FIG. 16 is a diagram showing the structure of conventional queue management.

FIG. 15 is a flow chart illustrating reference, addition, correction and erasure of a processing status of an examination file relative to the queue table.

For the reference to the queue table, a queue semaphore is acquired, and after the table reference, the queue semaphore is released. For the addition, correction and erasure relative to the queue table, a queue semaphore is acquired to make a backup copy of the queue table and perform the addition, correction and erasure. In this case, two or more works of addition, correction and erasure can be performed collectively, and the queue table reference work can be performed at the same time. After a backup copy of the queue table is erased, the queue semaphore is released.

For the addition of an examination file to the queue table, a queue semaphore is acquired and thereafter a new QID is issued and then added to the last line of the queue table to thereafter release the queue semaphore.

The queue table will be detailed. In order to simplify the description, the processing statuses are substituted by the words "UNDONE", "ON EXECUTING" and "DONE". However, in practice, the values "−1", "−2" and "−3" are used in place of these words. Each column represents a process to be performed on the background. The image processing processes a live image by using the live image processing parameters. Transfer processes 1 to 4 transfer the processed live image to an external apparatus which may be a server or a printer connected to a network, or an external portable storage medium directly connected by SCSI or the like. An erase process erases images such as live images and processed images already transferred and copied from the non-volatile storage unit. Each row of the queue table is hereinafter called a queue.

When a new examination file is entered into the image processing queue, "UNDONE" representative of that the process for the image is not still performed, is written in the columns of image processing, transfer processes 1 to 4 and erase process. "UNDONE" indicates that the process indicated in the column is not performed by any one of the background processing tasks. "ON EXECUTING" indicates that the process indicated in the column is now being executed by one background processing task. In this case, the task ID (TID) of the background processing task is written in the queue table. "DONE" indicates that the process indicated in the column is completed.

Figure 13B:
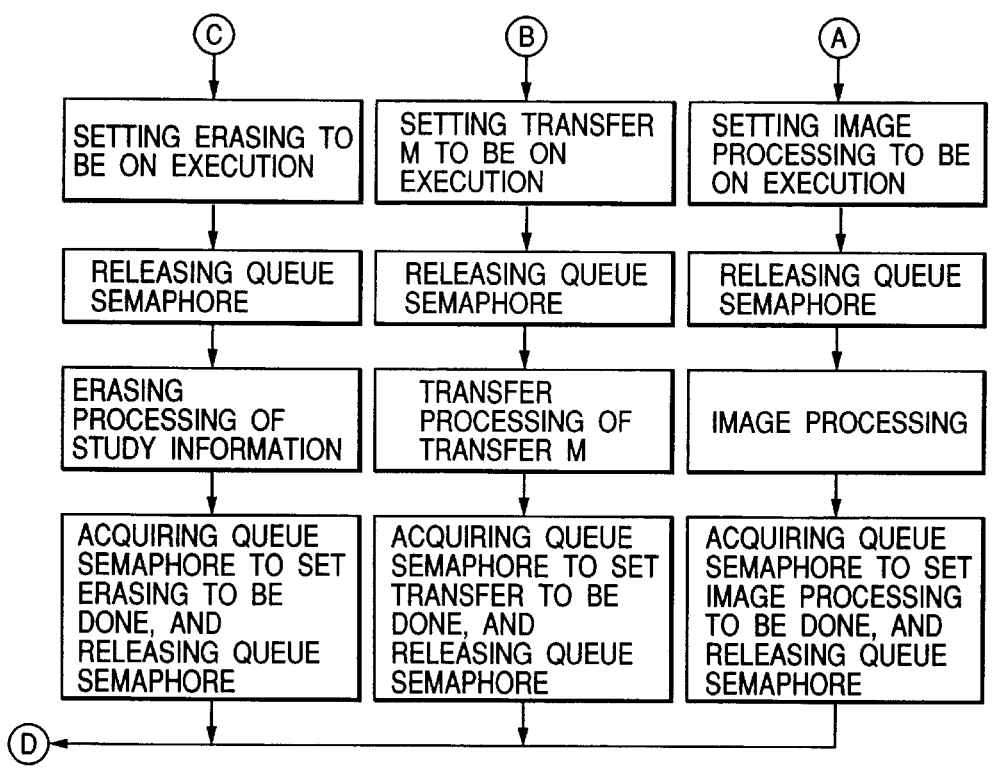
FIG. 13 which is comprised of FIGS. 13A and 13B are flow charts illustrating an operation of image processing, image transmitting and image erasing.

FIGS. 13A and 13B are flow charts illustrating how a plurality of background processing tasks having the same control method execute processes synchronously by referring to the queue table written with "DONE", "ON EXECUTING" and "UNDONE".

When the background processing task executes a process, the task is required to refer to the queue table. Since the queue table is rewritten by a plurality of background processing tasks and a signal operation processing task, an exclusive process called a semaphore process is performed.

When the background processing task executes a process, it acquires a queue semaphore. If the queue semaphore cannot be acquired, the background processing task stands by until another task releases the queue semaphore.

Next, a counter N for reading an N-th queue from the top of the queue table is set to "1". Then, information in the N-th queue is read.

If the N-th queue is present, the flow advances to the next step, whereas if not, the queue semaphore is released to return to the first step. If the N-the queue is present, the contents of the image processing column are checked. If the contents are "UNDONE", the image processing column in the N-th queue is set with "ON EXECUTING" and the task ID of the background processing task is written to thereafter release the queue semaphore.

The examination file written in the N-th queue is read to process the image of this examination. This image processing is characterized in that it is performed by using the live image processing parameters described earlier and that the image compression is performed after the irreversible compression rate of the image recorded in the image attribute is embedded in the image as a bit map. Namely, the image processing contains the processes up to the image compression process.

Figure 17:
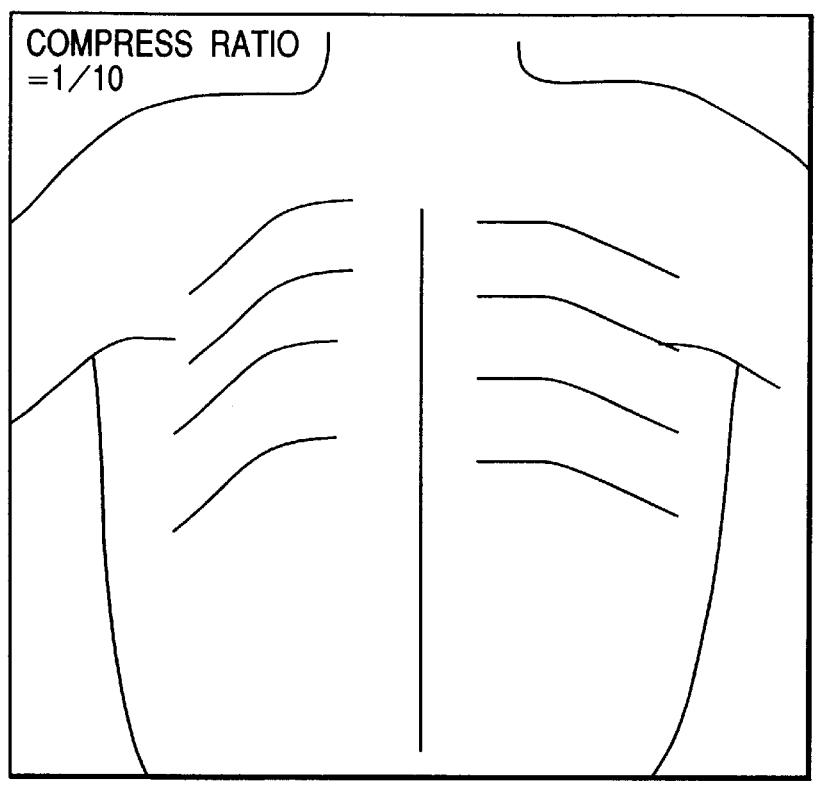
FIG. 17 is a diagram showing an example of an image whose compression rate is embedded as a bit map.

FIG. 17 shows an example of an image having an image compression rate embedded as a bit map. After the image processing, a queue semaphore is again acquired and "ON EXECUTING" is changed to "DONE" to thereafter release the queue semaphore to return to the first step. It is to be noted that since the queue semaphore is maintained released during the image processing, the background processing task other than the task executing the image processing or the operation processing task can acquire the queue semaphore to perform a process.

If the image processing column is "ON EXECUTING", the counter N is incremented by "1" to return to the third step shown in FIGS. 13A and 13B. If the image processing column is "DONE", a transfer counter M is set to "1" in order to execute the transfer processes 1 to 4. Next, the contents of the M-th transfer column are checked. If the contents are "UNDONE", the M-th transfer column in the N-th queue is set with "ON EXECUTING" and the task ID of the background processing task is written to thereafter release the queue semaphore.

The examination file written in the N-th queue is read and the M-th transfer process transfers the image of this examination. The M-th transfer process transfers the image to a predetermined destination in the system. After the transfer process, a queue semaphore is again acquired and "ON EXECUTING" is changed to "DONE" to thereafter release the queue semaphore to return to the first step. It is to be noted that since the queue semaphore is maintained released during the transfer process, the background processing task other than the task executing the transfer process or the operation processing task can acquire the queue semaphore to perform a process.

If the transfer process column is "ON EXECUTING", the flow stands by until the transfer process is completed. If the transfer process column is "DONE", the counter M is incremented by "1". If M is not larger than "4", the flow returns to the step shown in FIGS. 13A and 13B to complete the transfer processes 1 to 4. If M is larger than "4", it is checked whether all the transfer processes 1 to 4 are "DONE". If not, the counter N is incremented by "1" to return to the step shown in FIGS. 13A and 13B. This means that if there is even one transfer process under execution, a process for the next queue can be executed.

If all the transfer processes 1 to 4 are not "DONE", a counter N is increased by one and the flow returns to a predetermined position as shown in FIGS. 13A and 13B.

If all the transfer processes 1 to 4 are "DONE", the contents of the erase process column are checked. If the contents are "UNDONE", the erase process column of the N-th queue is set with "ON EXECUTING" and the task ID of the background processing task for executing the erase process is written to thereafter release the queue semaphore. The examination file written in the N-th queue is read and the erase process is performed for the image of this examination.

The erase process erases an examination file, a plurality of live image files designated by the examination file, and processed live image files, respectively stored in the non-volatile storage unit.

After the erase process is completed, a queue semaphore is again acquired and "ON EXECUTING" is changed to "DONE" to thereafter release the queue semaphore to return to the first step. It is to be noted that since the queue semaphore is maintained released during the erase process, the background processing task other than the task executing the erase process or the operation processing task can acquire the queue semaphore to perform a process.

If the erase process column is "ON EXECUTING", the counter N is incremented by "1" to return to the third step shown in FIGS. 13A and 13B. If the erase process column is "DONE", the N-th queue is erased from the queue table. When this queue is erased, the queues after this erased queue are raised by one row. Thereafter, the queue semaphore is released to return to the first step.

As described above, a plurality of tasks operate synchronously by using the queue table.

Figure 14B:
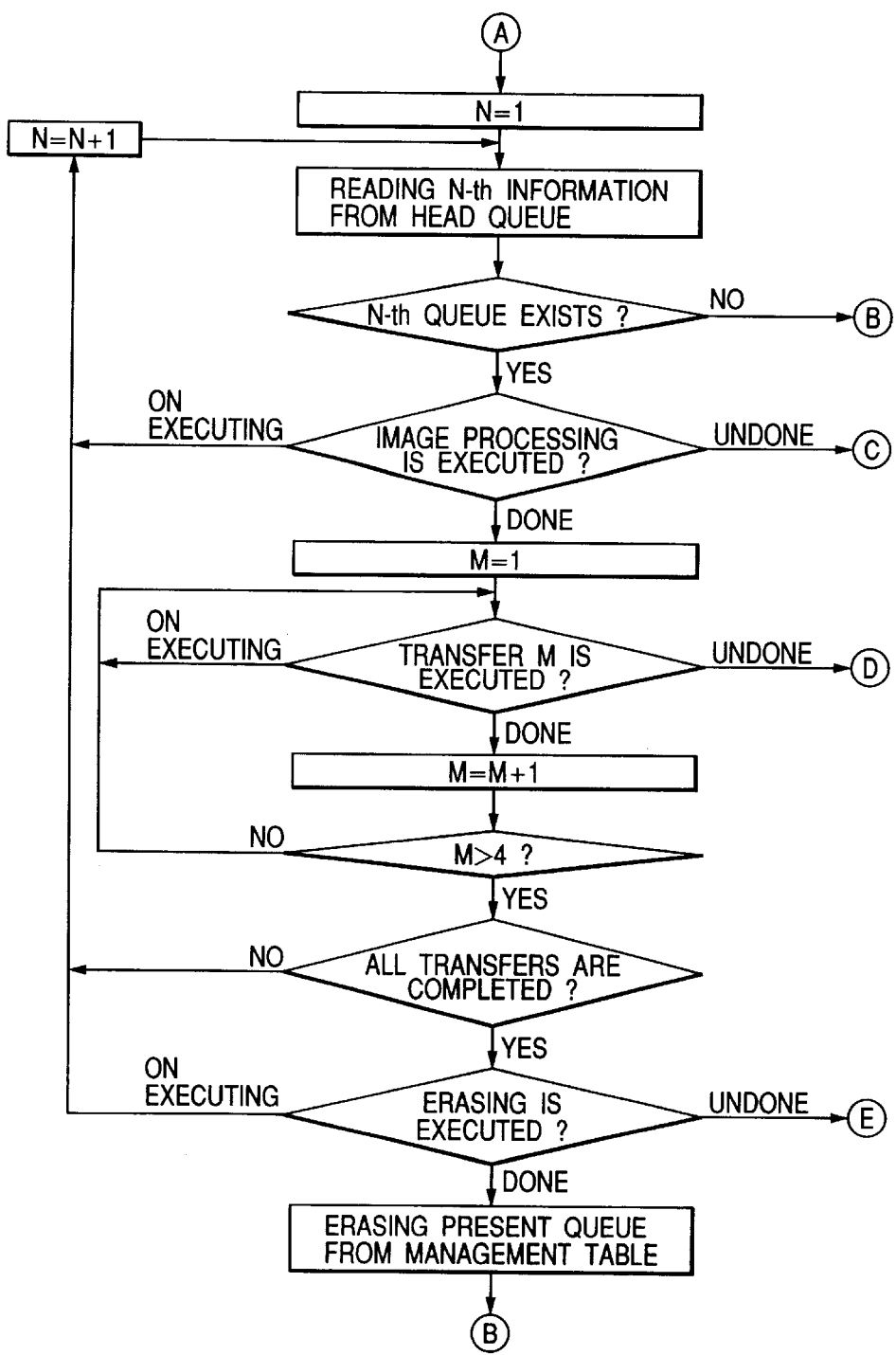
FIG. 14 which is comprised of FIGS. 14A, 14B and 14C are flow charts illustrating another operation of image processing, image transmitting and image erasing.
Figure 14C:
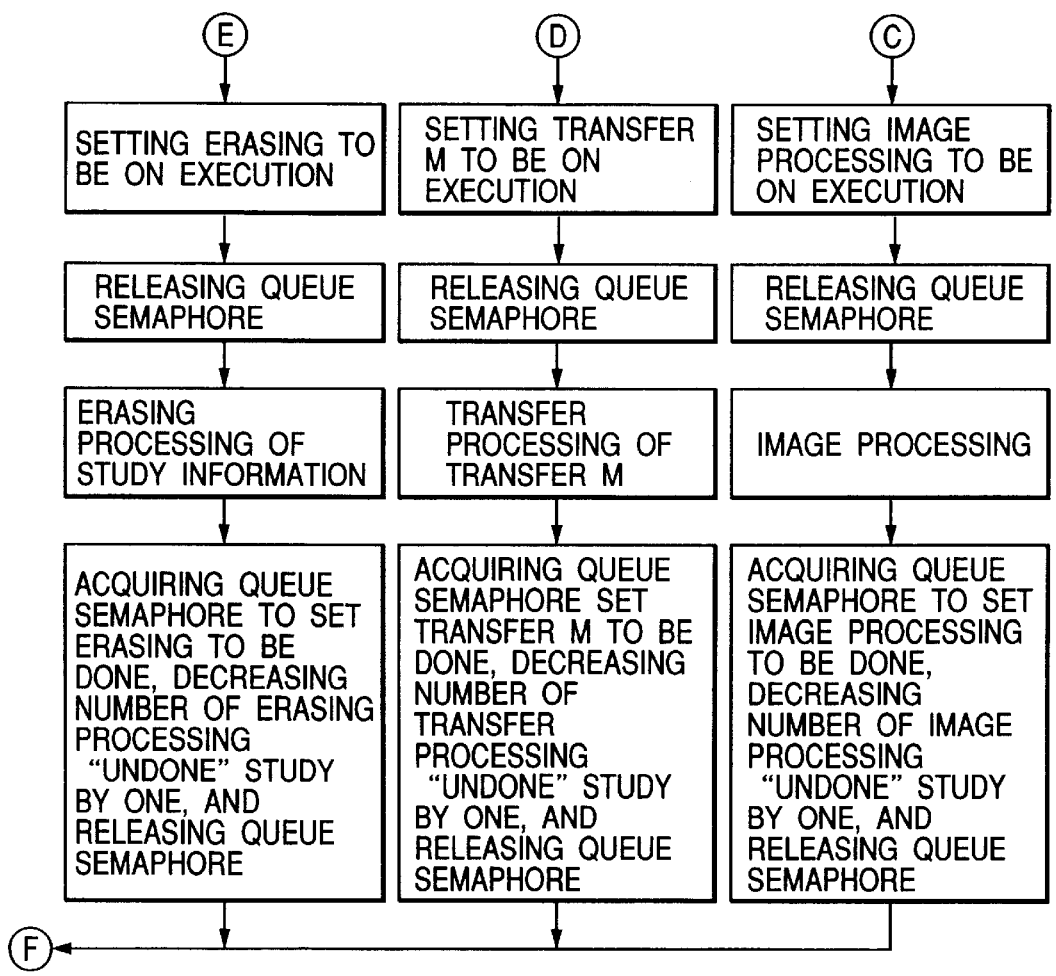

FIGS. 14A, 14B and 14C are flow charts illustrating an operation of the system capable of improving a process speed by storing information in RAM, the information determining whether the queue table in the non-volatile storage unit is to be accessed or not.

In this process shown in FIGS. 14A, 14B and 14C, it is assumed that when a new queue is added to the queue table, each variable to be stored in RAM is incremented by "1", the variable including the number of image processing "UNDONE" studies, the number of transfer process 1 "UNDONE" studies, the number of transfer process 2 "UNDONE" studies, the number of transfer process 3 "UNDONE" studies, the number of transfer process 4 "UNDONE" studies, and the number of erase process "UNDONE" studies.

Referring to FIGS. 14A, 14B and 14C, first a queue semaphore is acquired. If the number of image processing "UNDONE" studies is "1" or larger, it means that there is a queue whose image is to be processed. The flow advances to the step of N=1. If the number of image processing "UNDONE" is 0, a variable P is set to "1". If the number of transfer process P "UNDONE" studies is "1" or larger, it means that the transfer process is necessary so that the flow advances to the step of N=1. This process is performed by changing P from 1 to 4.

If the number of erase process "UNDONE" studies is "1" or larger, the flow advances to the step of N=1. In this embodiment, if the number of per-process "UNDONE" studies is "1" or larger, the flow advances to the step of N=1. The following steps are the same as those shown in FIGS. 13A and 13B. A different point is that after each process is completed, the number of per-process "UNDONE" studies is decremented by "1".

Since the queue table is stored in the non-volatile storage unit, if the system power is turned off inadvertently by the operator or it is turned off by some unknown reason, the system may become "ON EXECUTING" at the next setup even if there is no task under operation. In such a case, after the system power is turned on, if a backup copy of the queue table is present, the queue table is erased and the backup copy is changed to the queue table. Thereafter, all "ON EXECUTING" process statuses are changed to "UNDONE". In this manner, logic integrity can be maintained even after such a power turn-off.

As described above, according to this embodiment, when the exposure button is depressed in a predetermined time after the sensing part is set, an X-ray sensing is performed. If the exposure button is not depressed in a predetermined time, the operation of the solid state image pickup unit is automatically stopped. Accordingly, the operator is not required to control to turn on and off the solid state image pickup unit to facilitate the operator work.

When the patient information is entered, the solid state image pickup unit is made active. If the exposure is not performed for a predetermined period, a time-out occurs to make the solid state image pickup unit inactive. Accordingly, the life time of the solid state image pickup unit can be prolonged, the operator is unnecessary to turn on and off the solid state image pickup unit, and an image can be sensed at once at any time when necessary.

Furthermore, image processing parameters and sensing conditions are automatically determined in accordance with a selected sensing part. A conventional analog sensing routine work of an X-ray technical person includes to write examination information such as patient information and sensing information such as a sensing part, in a radiation record note. Such a record work is not necessary. The X-ray technical person is not required to perform a digital sensing work, and the analog sensing routine work can be performed with good workability without considering the image processing, the drive state of the solid state image pickup unit, and the like.

Only by setting a sensing part, the image processing and the drive state of the solid state image pickup unit can be changed. Patient information such as a patient name can be entered, before an examination, before or after all images are sensed. Therefore, workability and easy-to-use of the system can be improved.

Figure 18:
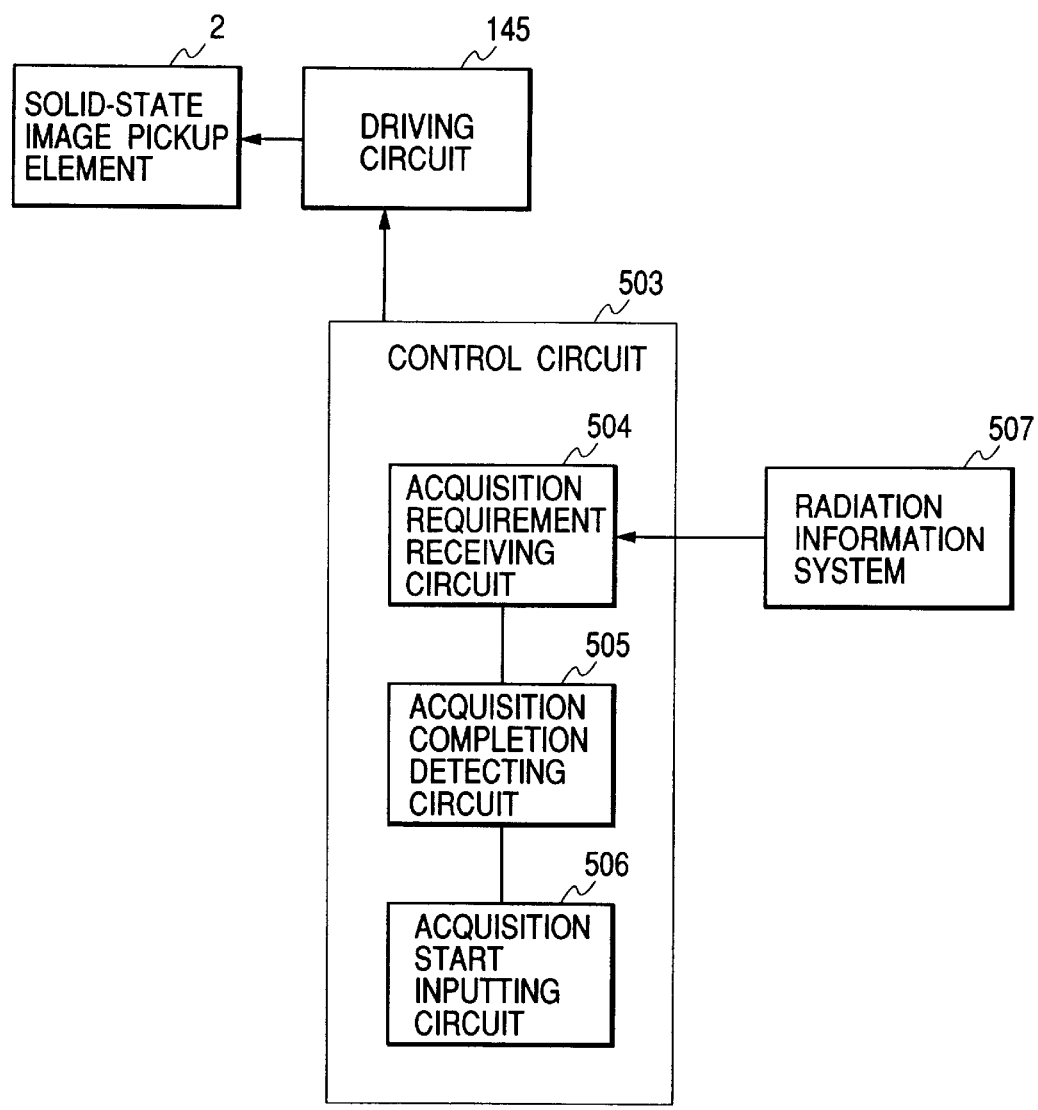
FIG. 18 is a diagram showing an X-ray image collecting system according to a second embodiment.

A second embodiment of the invention will be described with reference to the accompanying drawings. FIG. 18 is a schematic block diagram showing the main structure of the second embodiment.

Referring to FIG. 18, reference numeral 2 represents a solid state image pickup unit for visualizing a density distribution of an X-ray beam transmitted through a patient. In this embodiment, this solid state image pickup unit is an amorphous sensor silicon sensor, and its equivalent circuits are shown in FIGS. 1 and 2.

A driving circuit 145 sends a read signal to the solid state image pickup unit to sequentially read charges accumulated in each pixel. The driving circuit 145 has also the function of amplifying the read charges and A/D converting the charge signal which is transferred to an image memory unrepresented. The driving circuit 145 also controls to turn on and off an unrepresented power supply of the solid state image pickup unit 2 by using a control signal.

A control circuit 503 controls to make the driving circuit 145 enter acquisition enabled state (on) or an acquisition disabled state (off). The control circuit 503 is constituted of an acquisition request receiving circuit 504 for receiving an acquisition request from a radiation information system 507, an acquisition completion detecting circuit 505 for judging whether the requested sensing is completed, and an acquisition start inputting circuit 506.

Figure 19:
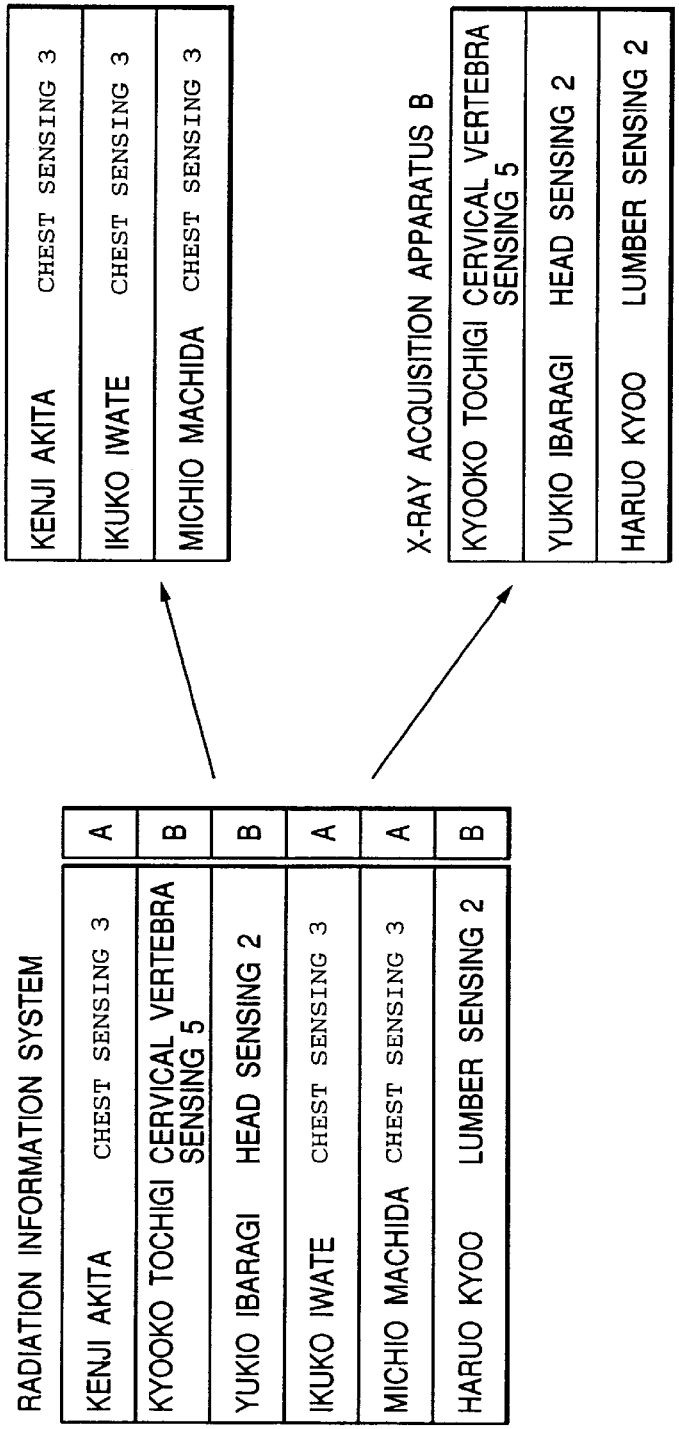
FIG. 19 is a diagram showing an sensing request list according to the second embodiment.

FIG. 19 shows an acquisition request list input to the radiation information system 507 or transferred from a hospital information system. The request list is divided into subsidiary lists in accordance with the resource state of a radiation department, and in the example shown in FIG. 19, it is divided in accordance with X-ray image modulities A and B. Patients may be allocated in a sequential order, or as in the example shown in FIG. 19, they are allocated to a chest acquisition room A and a bone imaging room B.

The X-ray image modulity A will be described. When any one of Kyooko TOCHIGI, Yukio IBARAGI and Haruo KYOO becomes a sensing preparatory state, i.e., visits the radiation department, a technician selects the patient by using the sensing start inputting circuit 506. The list at the X-ray image modulity B shown in FIG. 19 is displayed at the acquisition start inputting circuit 506, and the operator selects a proper one.

When the patient is selected by using the acquisition start inputting circuit 506, the control circuit 503 sends a signal to the driving circuit 145 to make it enter an enabled state. Alternatively, when a request from the radiation information system 507 is received at the sensing request receiving circuit 504, the control circuit 503 sends a signal to the driving circuit 145 to make it enter an acquisition enabled state. When the power of the entire system is turned on, the solid state image pickup unit is in a standby state.

For example, after five cervical images of Kyooko TOCHIGI are taken, images of either Yukio IBARAGI or Haruo KYOO will be taken. If the solid state image pickup unit is made in a standby state after images of Kyooko TOCHIGI are taken, it takes a time for the solid state image pickup unit to become stable and being able to sense the next patient. Therefore, in this example, it is assumed that images of either Yukio IBARAGI or Haruo KYOO are sensed immediately after Kyooko TOCHIGI and the solid state image pickup unit is not made into the standby state until the images of the remaining two patients are sensed.

When the sensing completion detecting circuit 505 detects that the requested image sensing is completed, the control circuit 503 sends a signal to the driving circuit 145 to make the solid state image pickup unit enter a standby state. The radiation information system sends an acquisition request at any time when there is an acquisition request from each diagnosis department. Therefore, if a new sensing request is received before the list becomes empty, the solid state image pickup unit is not made into a standby state even after images of the three patients are sensed. However, once the list becomes empty, the solid state image pickup unit is made into a standby state and is not made in an acquisition enabled state unless a new acquisition start request is supplied from the acquisition start inputting circuit 506.

The image collecting system of this embodiment will be described with reference to FIG. 20. Reference numeral 101 represents an X-ray room, reference numeral 102 represents an X-ray control room, and reference numeral 103 represents a diagnosis room. The overall operation of the image collection system is controlled by a system control unit 110. The main functions of the system control unit 110 will be described in the following.

The system control unit 110 gets or receives a sensing request from the radiation information system 507, and the operator gives an instruction via an operator interface 111. The solid state image pickup unit 2 is changed from the standby state to the sensing enabled state in response to a reception of the sensing request or in response to an instruction via the operator interface. In this case, if the request list becomes empty after the requested sensing images are sensed, the solid state image pickup unit is made in the standby state. The operator interface 111 includes the acquisition start inputting circuit 506 shown in FIG. 18. The system control unit 110 includes the acquisition request receiving circuit 504 and sensing completion detecting circuit 505.

The operator interface 111 includes a touch panel of a display unit, a mouse, a keyboard, a joy stick, a foot switch, and the like. The sensing conditions (such as an still image, a moving image, an X-ray tube voltage, an X-ray tube current, and an X-ray exposure time), an acquisition timing, an image processing condition, a patient ID, a sensed image processing method, and the like can be set via the operator interface 111. However, all of these are not required to be entered because of most of them are transferred from the radiation information system. An important work of the operator is a work of checking the sensed image. Namely, the operator checks whether the sensing angle is correct, whether the patient does not move, or whether the image processing is proper.

The system control unit 110 supplies the acquisition conditions instructed by the operator 105 to an acquisition control unit 214 which controls an X-ray image acquisition sequence. In accordance with the acquisition conditions, the acquisition control unit 214 drives an X-ray generation apparatus 120 having a radiation source 211, an acquisition bed 130 and an X-ray detector 140 to pick up image data which is transferred to an image processing unit 10 whereat it is processed in accordance with the image processing designated by the operator, and displayed on a display unit 160. At the same time, fundamental image processing data is stored in an external storage unit 161.

In accordance with the instruction from the operator 105, the system control unit 110 further performs a reproduced image processing, a reproduced image display, transfer and storage of image data to and in an apparatus on a network, an image display, an image print, and the like.

Next, the sequential flow of a signal will be described.

The X-ray generation apparatus 120 includes an X-ray tube 121 and a X-ray aperture 123. The X-ray tube 121 is driven by a high voltage power source 124 under the control by the acquisition control unit 214 to radiate an X-ray beam 125. The X-ray aperture 123 is driven by the acquisition control unit 214 to shape the X-ray beam 125 so as not to radiate an unnecessary part of the patient, in accordance with a change in the acquisition area. The X-ray beam 125 is directed toward a patient 126 lying on the sensing bed 130 which is transparent to X-rays. The acquisition bed 130 is driven in accordance with an instruction of the sensing control unit 214. The X-ray beam 125 passes through the patient 126 and sensing bed 130 and is applied to the X-ray detector 140.

The X-ray detector 140 includes a grid 141, a scintillator 142, the solid state image pickup unit 2, an X-ray exposure amount monitor 144 and a driving circuit 145. The grid 141 suppresses the influence of X-ray scattering to be caused by transmission through the patient 126. The grid 141 is made of X-ray low and high absorption materials. For example, the grid 141 has a stripe structure of Al and Pb. The grid 141 is oscillated in response to an instruction from the acquisition control unit 214 so that moire is not generated which may be generated when the lattice ratio between a photodetector array 8 and grid 141 takes a certain value.

In the scintillator 142, the source material of a fluorescent member is activated by high energy X-rays, and fluorescent light of a visible range is generated by recombination energy. The fluorescent light is generated by the source material itself such as $CaWO_4$ and $CdWO_4$ or by radiative materials activated in the source material such as CsI:Tl and ZnS:Ag.

The photodetector array 8 is disposed near the scintillator 142. The photodetector array 8 converts a photon into an electric signal. The X-ray exposure amount monitor 144 monitors an X-ray transmission amount. The X-ray exposure amount monitor 144 may directly detect X-ray by using a silicon crystal photosensor or the like or detect light from the scintillator 142. In this example, visible light (proportional to X-ray exposure amount) transmitted through the photodetector array 8 is detected with amorphous silicon photodetector elements formed on the bottom of the substrate of the photodetector array 8, and the detected visible light information is supplied to the acquisition control unit 214. In accordance with this information, the acquisition control unit 214 drives the high voltage power source 124 to intercept or control the X-ray. Under the control of the acquisition control unit 214, the driving circuit 145 drives the photodetector array (flat panel sensor) 8 to read a signal from each pixel. The photodetector array 8 and driving circuit 145 have the same structure as that described with reference to FIGS. 1 and 2.

An image signal from the X-ray detector 140 is transferred from the X-ray room 101 to the image processing unit 10 in the X-ray control room 102. In this case, the image data may be transferred abnormally because of large noises caused by the generation of X-rays in the X-ray room 101. It is therefore necessary to make the transfer path have a high noise resistance. It is preferable therefore to use a transfer path provided with an error correction function or a transfer path of a shielded pair twisted cable or optical cable using a differential amplifier. The image processing unit 10 switches between display data in accordance with an instruction from the acquisition control unit 214 (this will be later detailed). The image processing unit 10 may also perform image data correction, spatial filtering, recursive processing, respectively in real time, gradation processing, scattering correction, DR compression and the like.

The processed image is displayed on the display unit 160 via a display adapter 151. At the same time when the real time image processing is performed, the fundamental image with only data correction is stored in a high speed storage unit 161. The high speed storage unit 161 has preferably a large capacity, a high speed, and a high reliability, for example, it is a hard disk array such as RAID. In accordance with an instruction by the operator, the image data stored in the high speed storage unit 161 is also stored in an external storage unit. In this case, the image data is reconfigured before it is stored in the external storage unit, so as to satisfy a predetermined specification such as IS & C. The external storage unit may be a magnetooptical disk 162, a hard disk in a file server 170 on LAN, or the like.

The image collecting system may be connected to a LAN via a LAN board 163 and has data compatibility with HIS. Not only a plurality of image collecting systems are connected to LAN, but also other apparatuses are connected to LAN, such as a monitor 174 for displaying moving and still images, the file server 170 for filing image data, an image printer 172 for printing out an image on a film, and an image processing terminal 173 for performing a complicated image processing and supporting diagnosis. This image collecting system outputs image data in accordance with a predetermined protocol such as DICOM. By using a monitor connected to LAN, real time remote diagnosis by a doctor can be performed during X-ray image sensing.

As described above, according to this embodiment, the solid state image pickup unit is made in an acquisition enabled state in response to an acquisition request from the radiation information system 507 or in response to an operator instruction via the operator interface 111. It is therefore very easy to operate this system. If the request list becomes empty after the acquisition request is responded, the solid state image pickup unit enters the standby mode. It is therefore possible to shorten a wasteful use time, reduce power consumption and prolong the life time of the solid state image pickup unit. Heat generation of the driving circuit 145 can be minimized.

In the first and second embodiments, the standby state (non-drive state) includes to enter the low consumption current mode and to turn off the power supply.

The third embodiment of the invention will be described with reference to the accompanying drawings.

FIG. 3 is a block diagram showing the structure of an X-ray image collecting system.

The image collection apparatus 100 receives ordering information from an external network. This embodiment has two modes. In one mode, at the same time when ordering information is received, a sensing start work begins automatically. In the other mode, the sensing start work begins after the received ordering information is supplied to a user interface. Both modes will be later described with reference to FIG. 21 and following figures, and the detail description is omitted herein.

First, an operator guides an object between the solid image pickup unit 2 and X-ray tube 3. Next, in order to set a sensing part, the operator depresses the part setting button in accordance with the ordering information. In response to this operation, the apparatus 100 automatically generates the solid state image pickup unit drive control signal to apply voltage to the solid image pickup unit 2 for the preparation of image sensing by the unit 2.

A grid operation speed parameter is adjusted. The exposure button 7 is used for issuing a trigger of generating an X-ray beam. An exposure signal a issued by the exposure button 7 is input to the image reading control unit 5 of the image collection apparatus 100. The image reading control unit 5 checks from the state of the drive notification signal whether the unit 2 can receive an X-ray beam and sense an image. If the state is satisfied, the image reading control unit 5 generates the exposure permission signal to turn on the exposure permission switch so that the exposure signal A is supplied to the X-ray generation apparatus control unit 9 as an exposure signal B. The exposure signal A is generated upon actuation of a switch called a second switch of the exposure button. The exposure signal B is provided to the X-ray generation apparatus control unit 9.

At the same time, the grid 10 starts operating to set an optimum speed. After the X-ray exposure is thus prepared, the x-ray generation apparatus control unit 9 generates the exposure signal C so that an X-ray beam is radiated from the X-ray tube 3. An X-ray transmitted through the object 1 is input as an image to the solid state image pickup unit 2 via the grid 10 and scintillator 11. This image is read out to be digitalized by the A/D converter 40, and then transferred to the image reading control unit 5.

The image control reading control unit 5 is managed by CPU 13. CPU 13 is connected via the bus 20 to RAM 14, ROM 15, LAN/IF 16, DISK/IF 17, control panel, non-volatile storage unit 18, user IF unit 19 and the like. In this embodiment, the non-volatile storage unit 18 is a hard disk. The user IF unit 19 has the display 4, keyboard, and mouse 21 for the interface with a user. It is apparent that a touch panel can be used for user interface. The image input to the image reading control unit 5 is temporarily stored in RAM 14 to be subjected to various image processing by CPU to be later described.

Figure 21:
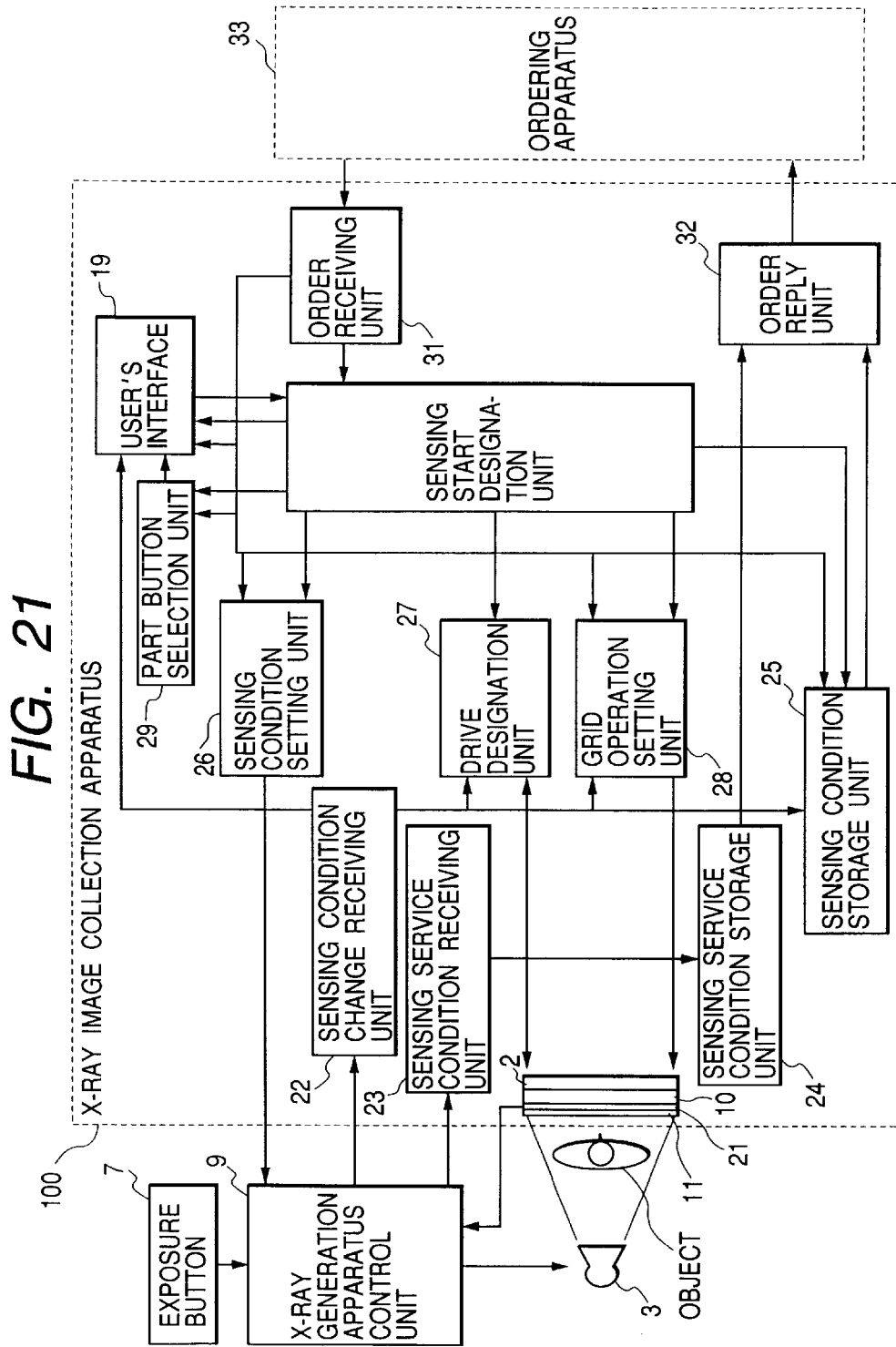
FIG. 21 is a functional block diagram of an X-ray image collecting system according to a third embodiment of the invention.

FIG. 21 is a functional block diagram of the X-ray image collection apparatus.

An order receiving unit 31 receives ordering information from an ordering apparatus 33. When the ordering information is received, a sensing start designation unit 30 is notified of an order arrival. In this embodiment, the sensing start designation unit 30 provides two modes. In one mode, at the same time when ordering information is received, a sensing start work begins automatically. In the other mode, the sensing start work begins after the received ordering information is supplied to a user interface. In the latter mode in particular, by using a user interface unit 18, a list of received orders can be displayed and a desired order can be selected from this list. In this case, prior to receiving the ordering information, it is necessary to issue a transmission request to the ordering apparatus 33 in order to receive the order list.

In both the modes, in the sensing start work, the order reception unit 31 analyzes the order and supplies personal information of a patient such as the name and year, month and day of birth as well as the sensing start designation to the user interface unit 19. Since the name of the patient is displayed on the user interface unit 19, this can be used for identification of the patient.

Next, part information of the first part ordered as well as the sensing start designation is supplied from the order receiving unit 31 to a part button selection unit 29.

The part information of the first part ordered includes setting sensing time which is set by the ordering apparatus to the X-ray generation apparatus. A moving speed of the grid is determined based on this setting sensing time. In case of that the setting sensing time is not supplied, setting sensing time which set and stored for each part button designated by the part button selection unit is used for setting.

The part button selection unit 29 allows the user interface unit 19 to select the corresponding part button. In accordance with the ordered sensing information, the user interface unit 19 displays the sensing condition. Although it will become apparent from the following description, immediately after the ordered first part is sensed, the sensing process for the second part starts in accordance with the second part information.

Next, the order reception unit 31 sends the sensing condition and sensing start designation to a sensing condition setting unit 26. In accordance with the ordered sensing condition, the sensing condition setting unit 26 sets the sensing condition to the X-ray generation apparatus control unit 9, for example, setting an X-ray tube voltage, a focus length, an image size and the like.

Subsequently, the order receiving unit 31 sends the sensing condition and the sensing start designation to a drive designation unit 27. The drive designation unit 27 applies a voltage to the solid state image pickup unit to set it into a driving state. This driving state is not a sensing state but a state in contrast to a state in which a voltage required to collect images is not applied in order to provide long life to the solid state image pickup unit. In the driving state, passage of one minite without a sensing operation generate time-out of the driving state and then the solid state image pickup unit is set into a non-driving state.

Next, the sensing condition and sensing start designation are sent to the drive designation unit 27 from the order receiving unit 31. A grid operation setting unit 28 determines a predetermined grid speed parameter in accordance with the sensing part information and the like. For example, for a sensing part having a long exposure time, the grid speed is lowered, whereas for a sensing part having a short exposure time, the grid speed is raised.

Next, the sensing condition and sensing start designation are sent to a sensing condition storage unit 25 from the order receiving unit 31. In this example, in order to manage sensing history, data is stored in RAM and hard disk of the system.

Next, the operation to be executed when the X-ray generation apparatus control unit 9 changes the tube setting, will be described.

In this embodiment, the X-ray generation apparatus control unit 9 can set sensing conditions such as a tube voltage, focal length and size different from the ordered sensing condition, in accordance with the health state of a patient set by a technician. In this case, a sensing condition change receiving unit 22 of the X-ray image collection apparatus 100 receives a change in the sensing condition. Then, the drive designation unit, grid operation setting unit 28 and sensing condition storage unit 24 operate again in the manner described previously because of resetting the sensing condition. The changed sensing condition is displayed on the user interface unit 18.

As the exposure button 7 is depressed, an X-ray beam is emitted from the X-ray tube 3. The data flow in this case is illustrated in FIG. 13. In practice, signals are supplied to the X-ray image collection apparatus 100 to generate control signals for the grid operation and solid state image pickup unit 2.

As the operator depresses the exposure button 7, an X-ray beam is generated and an image is taken. Thereafter, a sensing service condition such as a sensing time and a mAs value is generated by the X-ray generation apparatus control unit 9. This sensing service condition is received by a sensing service condition receiving unit 23 and sent to a sensing service condition storage unit 24. In this example, in order to manage sensing history, data is stored in RAM and hard disk of the system.

After one sensing operation is completed, a next sensing operation starts to repeat the above-described operations.

After an examination of a single or a plurality of sensing operations is completed, data in the sensing service condition storage unit 24 and sensing condition storage unit 25 is supplied to an order reply unit 32. In accordance with a communication protocol determined with the ordering apparatus 33, the order reply unit 32 informs the ordering apparatus 33 of a completion of the examination. In this case, the ordering apparatus is notified of the sensing condition and sensing service condition.

One aspect of this embodiment is that the X-ray generation apparatus control unit 9 is provided to activate the solid state image pickup unit 2. Therefore, even if the unit 2 is disabled by a time-out of one minute, the unit 2 can be enabled by the parameter change designation from the X-ray generation apparatus control unit 9. Even if the parameter is the same before and after the change, the X-ray generation apparatus control unit 9 generates the change designation. With this function, the sensing can be performed even if the operator does not look at the display screen of the X-ray image collection apparatus 100.

Figure 22:
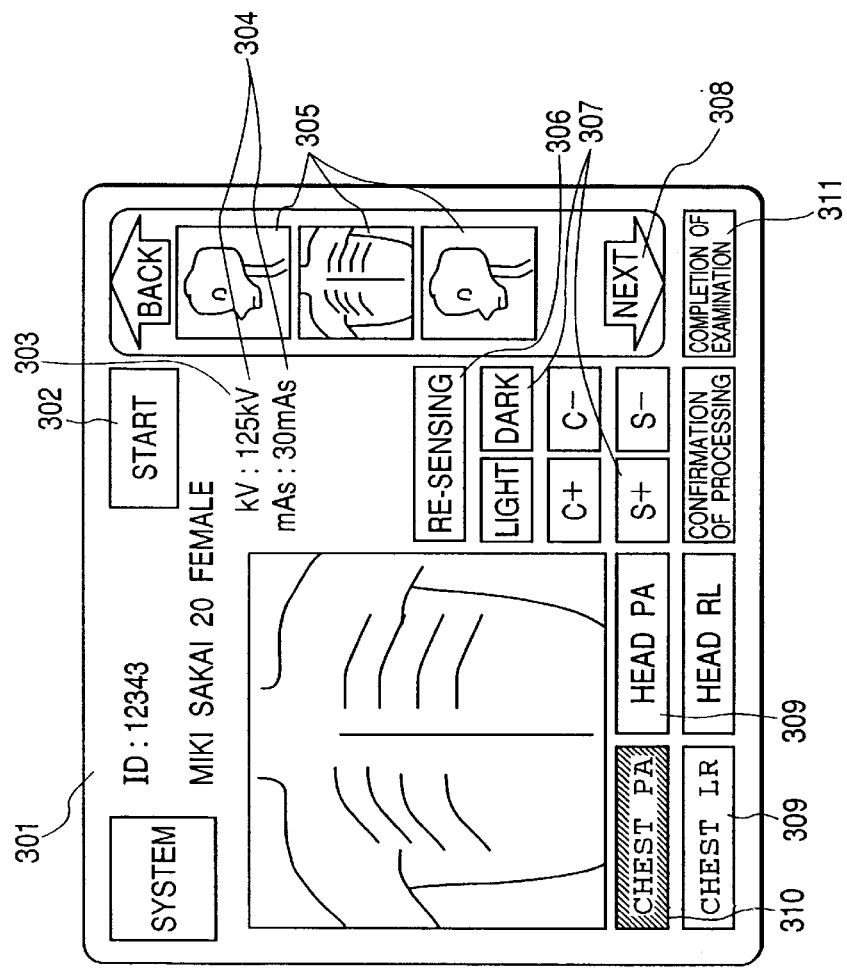
FIG. 22 is a diagram showing an example of a display screen of a display unit according to the third embodiment of the invention.

FIG. 22 is a diagram showing an example of a display screen of the display unit 4 according to the embodiment of the invention.

As an operator depresses the exposure start button 302 in order to sense an image, a transmission request is sent to the ordering apparatus 33 to receive an order list. The received order list is displayed to allow the operator to select an order from the order list. If the order list transmission request is not sent and an order is supplied from the ordering apparatus 33 to the X-ray image collection apparatus 100, the sensing start work begins by using the received ordering information. As the sensing work starts, the first sensing part "CHEST PA" button becomes of a selection state as indicated at 310. As the sensing condition, a tube voltage of 125 kV is displayed. This voltage value can be changed by the X-ray generation apparatus control unit 9 and the changed voltage value is displayed in real time. Thereafter, a sensing operation is performed, and as the sensing service conditions, a value of 30 mAs is displayed on the user interface. After all the sensing operations are completed, an examination completion button 311 is depressed or the operation automatically stops by a time-out process. After the examination completion, as described earlier, the sensing condition and sensing service condition are returned to the ordering apparatus 33 and the collected images are transferred to the external via the network.

In the above description, images are collected in accordance with the ordering information. In the examination, the designated parts are sequentially sensed under designated conditions. A sensing operation may fail. In many cases, this failure results from a motion of a patient. An image of a moving patient results in an image with blurred portions and reliable diagnosis is impossible.

An order from HIS does not require, however, all collected images before and after re-sensing, but in many cases, only one image of a particular part re-sensed at a particular condition is required. This embodiment meets such a requirement.

Figure 23:
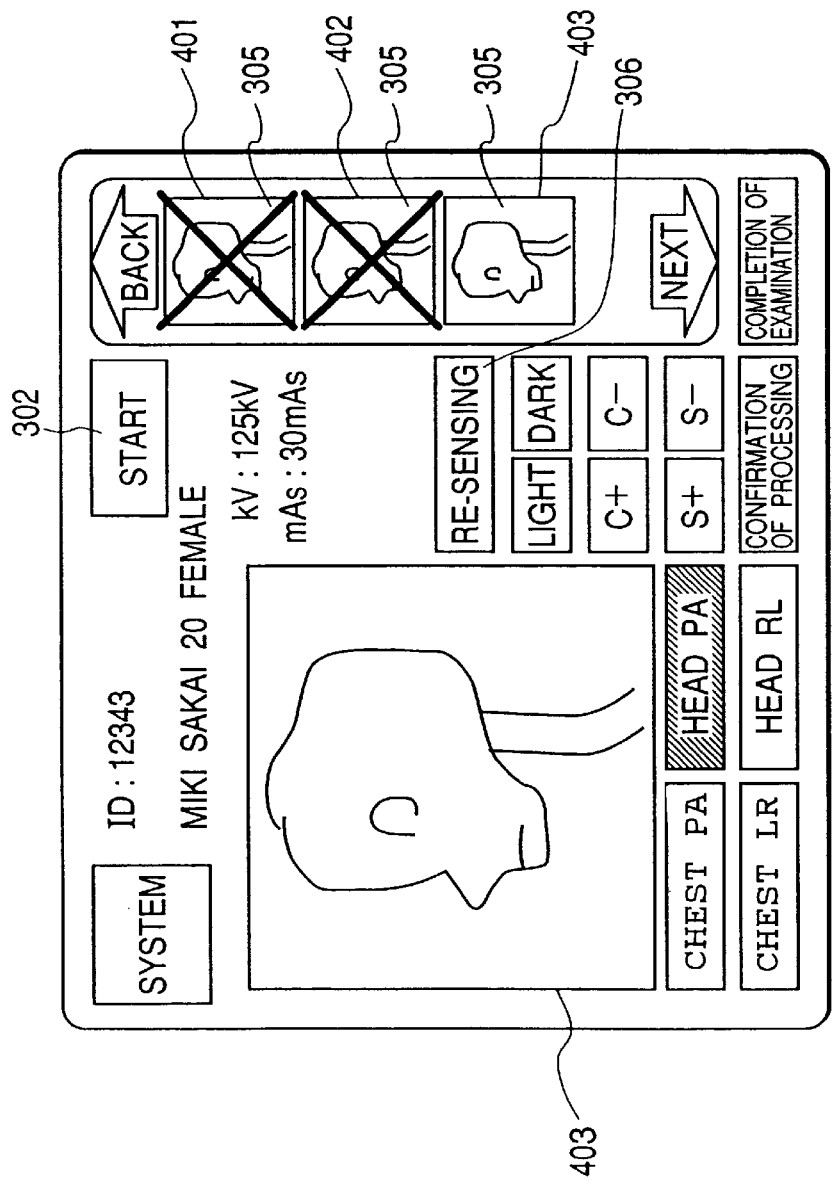
FIG. 23 is a diagram showing a display screen of the display unit after re-sensing.

FIG. 23 is a diagram showing the display screen of the display unit after the re-sensing.

If a head image has a blurred portion and re-sensing becomes necessary, a re-sensing button 306 is depressed. Then, the sensing ready state in the same condition starts. In this case, although the same condition is generally used, if the technician judges from the body of a patient and the like that the same condition could result in poor sensing, the sensing condition may be changed.

As the exposure button 7 is depressed for re-sensing, a re-sensed image is displayed as shown in FIG. 23. In the default state, the already sensed image is replaced by the re-sensed image, and the already sensed image is affixed with by a cross mark. In the example shown in FIG. 23, the re-sensing operation was performed twice.

There is a case that the operator performs a re-sensing operation several times. The last re-sensed image is not necessarily the image suitable for the order. In this case, the already re-sensed image is selected with the mouse, this selected image becomes a representative image, its cross mark is deleted, and the last re-sensed image is added with the cross mark. Namely, only the selected image is used as the image suitable for the order and the other images are considered as improper images.

All re-sensed images are stored in the non-volatile storage unit shown in FIG. 3 so that the image other than the image suitable for the order can be retrieved later and transmitted to the external.

Figure 24:
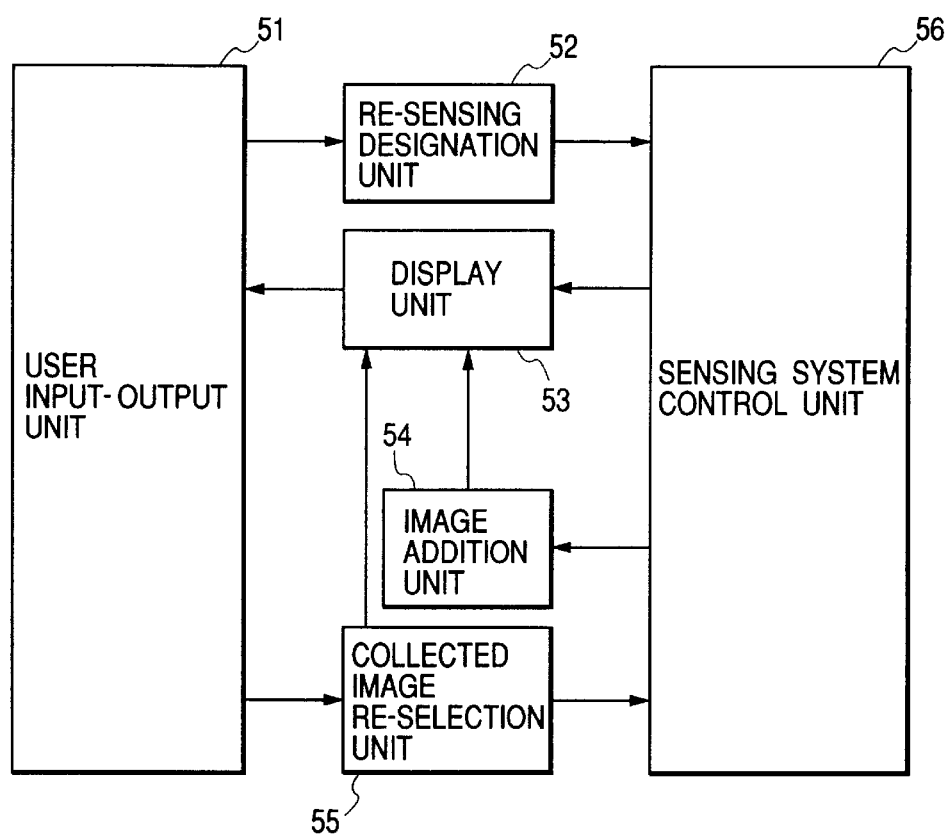
FIG. 24 is a functional block diagram illustrating a re-sensing process of the X-ray image collecting system according to the third embodiment of the invention.

FIG. 24 is a functional block diagram illustrating the re-sensing process of the X-ray image collection apparatus.

As an operator depresses the re-sensing button 306 to re-sense the image, this is notified to a user input/output unit 51 and via a re-sensing designation unit 52 to a sensing system control unit 56 which controls the sensing. The sensing system control unit 56 prepares for the sensing and executes the sensing operation when the operator depresses the exposure button 7 not shown in FIG. 24.

The sensed image is passed via an image addition unit 54 to a display unit 53. The display unit 53 displays the image on a display screen via the user input/output unit 51. The addition image is an image added to the overview list.

When the user input/output unit 51 re-selects the representative image from the re-sensed image group, this is notified to a collected image re-selection unit 55, and to the display unit 53 and sensing control unit 56. The display unit 53 deletes or adds the cross mark, and the sensing system control unit 56 retains the representative image among the re-sensed image group. After the examination completion, only the representative image is transmitted over the network.

Next, the image re-sensing process will be described with reference to the flow charts shown in FIGS. 30 to 32.

Figure 30:
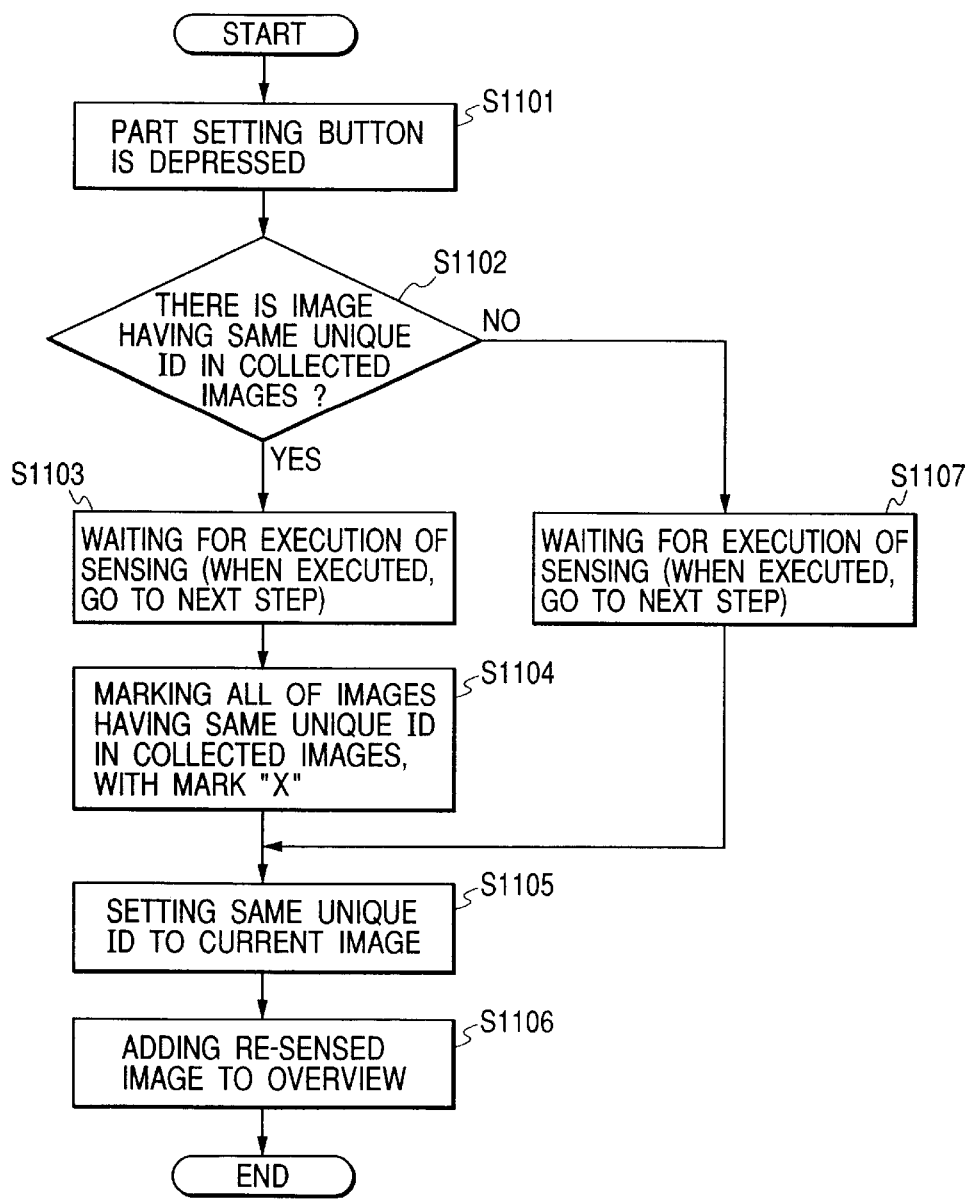
FIG. 30 is a flow chart illustrating a re-sensing process in response to a part setting button 309.

FIG. 30 is a flow chart illustrating the re-sensing process to be executed in response to actuation of the part setting button 309.

At Step S1101, it is judged whether the part setting button 309 is depressed. If depressed, the flow advances to Step S1102 whereat it is judged whether there is an image having the unique ID in the already sensed and collected images. If there is such an image, the flow advances to Step S1103, whereas if not, the flow advances to Step S1107. The unique ID is information for identifying sensing information such as the patient name, sensing part, sensing direction and sensing condition.

At Step S1103 the process enters a sensing execution standby state. As an image is sensed, the flow advances to the next Step S1104. At Step S1104 the process also enters the sensing execution standby state. As an image is sensed, the flow advances to the next Step S1105.

At Step S1104 all images having the same unique ID among the already collected images are affixed with the cross mark. This state corresponds to FIG. 23 in which the cross mark is affixed to the already collected images 1 and 2. Next, at Step S1105 the presently sensed image, i.e., the re-sensed image 403 shown in FIG. 23, is set with the unique ID same as those of the already collected images 1 and 2. Next, at Step S1106, the re-sensed image is displayed on the overview 305 as shown in FIG. 23 to thereafter terminate the re-sensing process.

Next, with reference to FIG. 31, the re-sensing process to be executed upon a re-sensing designation will be described.

Figure 31:
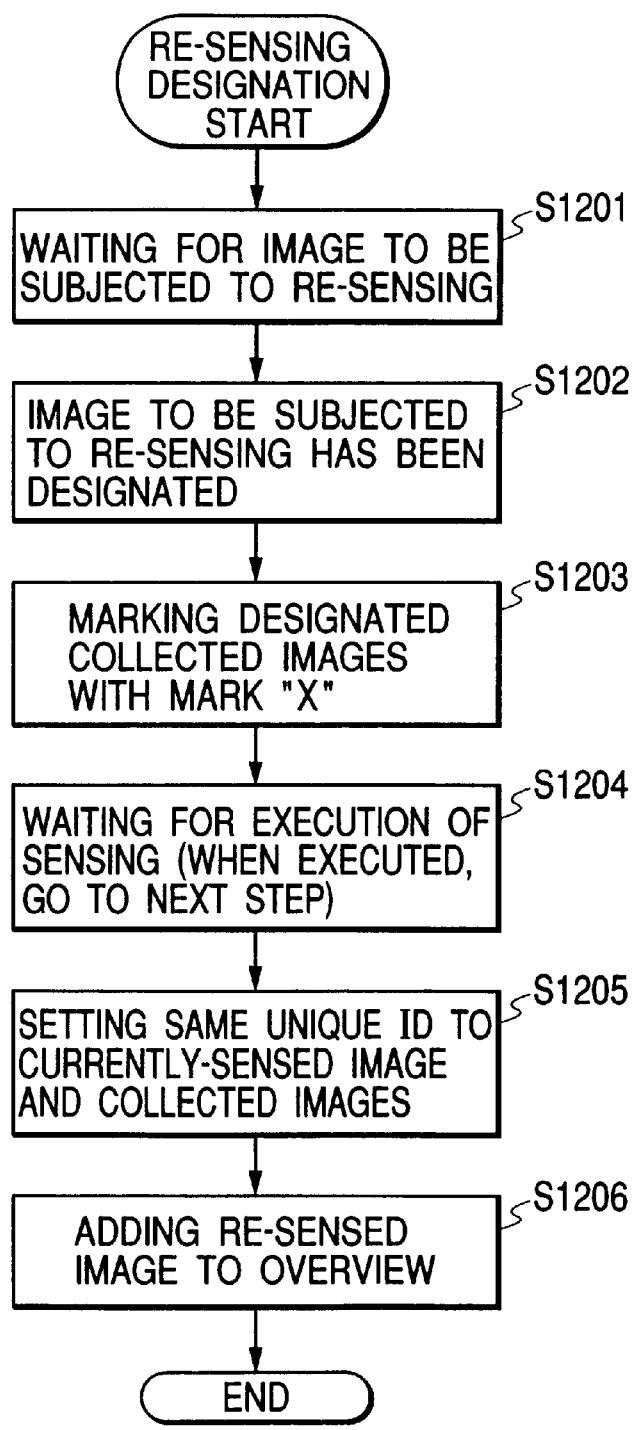
FIG. 31 is a flow chart illustrating a re-sensing process in response to a re-sensing designation.

In the flow chart shown in FIG. 31, the process starts when the re-sensing designation is given by the re-sensing button 306 or the like. At Step S1201 the process enters a standby state for waiting for a re-sensing object image. When the re-sensing object image is displayed on the display unit 4, the flow advances to Step S1202 whereat it is judged whether the re-sensing object image is selected from those re-sensing object images displayed at Step S1201. If selected, the flow advances to the next Step S1203 whereat the designated re-sensing object image, i.e., already collected image is affixed with the cross mark. This state corresponds to FIG. 23.

Next, at Step S1204 the process enters the re-sensing execution standby state. As an image is sensed, the flow advances to Step S1205 whereat the same unique ID is affixed to the already collected images and re-sensing image. The unit ID is similar to that described with FIG. 30, and the description thereof is omitted. Next, at Step S1206, the re-sensed image is displayed on the overview 305 as shown in FIG. 23 to thereafter terminate the process.

Figure 32:
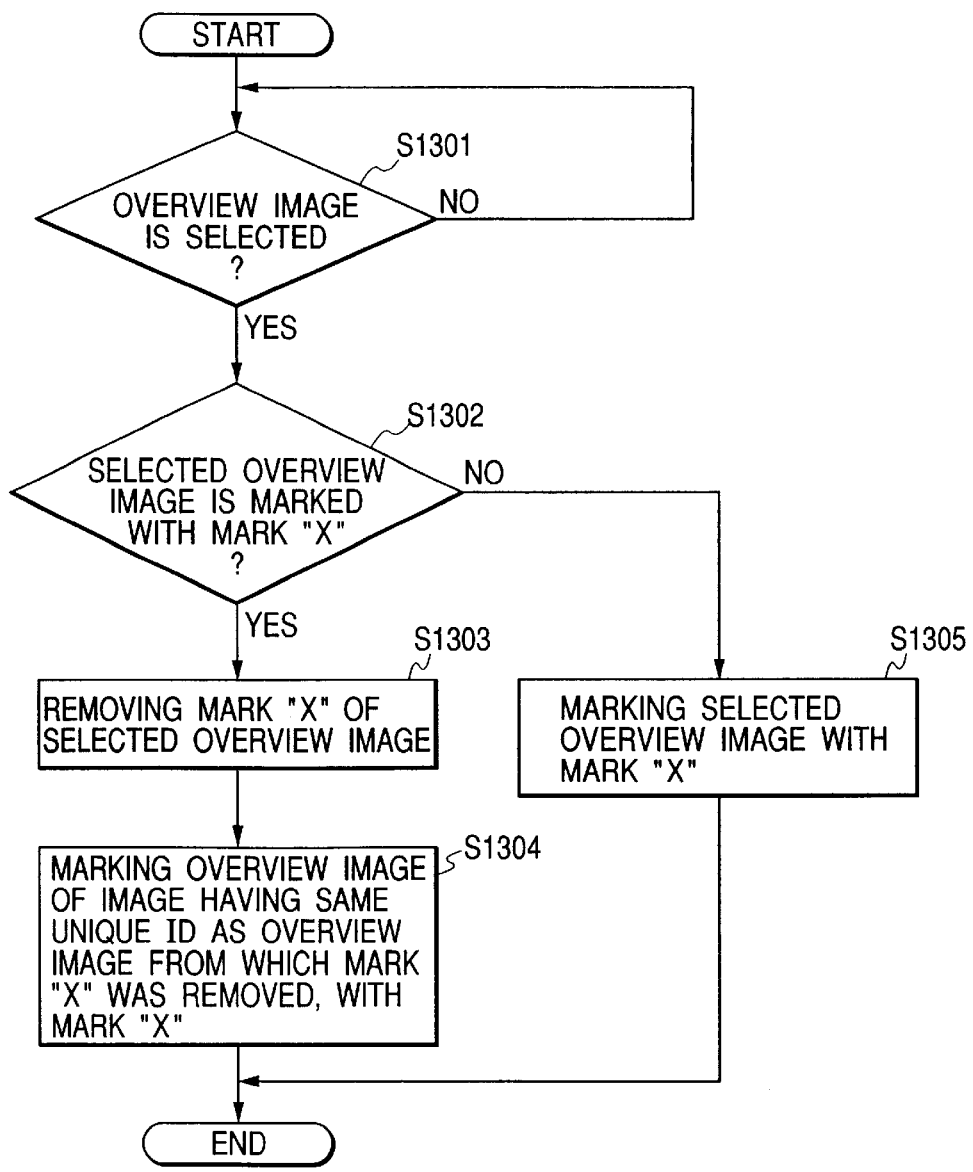
FIG. 32 is a flow chart illustrating a process of selecting an overview image.

FIG. 32 is a flow chart illustrating the process of selecting an overview image.

The process illustrated in FIG. 32 is executed after the re-sensing process illustrated in FIGS. 30 and 31. The details of this process will be given in the following.

At Step S1301 it is checked whether any one of the overview images 305 such as shown in FIG. 23 is selected. If selected, the flow advances to Step S1302 whereat it is checked whether the selected overview image has the cross mark. If the cross mark is affixed, the flow advances to Step S1303, whereas if not, the flow advances to Step S1305. At Step S1303 the cross mark is affixed to the selected overview image. At Step S1304 the image having the same unique ID as the overview image affixed with the cross mark at Step S1303 is searched, and the cross mark is affixed to the overview image having the same unique ID. With these processes, only one image not affixed with the cross mark can be selected from the overview images having the same unique ID and the selected one image only can be transmitted to the external. In this embodiment, although only one image is selected, it is obvious that a plurality of images may be selected and transferred to the external.

If it is judged at Step S1302 that the selected overview image is not affixed with the cross mark, the process advances to Step S1305 whereat the cross mark is affixed to the selected overview image.

As described with the flow chart shown in FIG. 32, it is possible to select an image suitable for examination from a re-sensed image group and transmit it to the external. The re-sensing process can be executed relatively easily. For example, even the case wherein the already sensed image is better than the re-sensed image can be dealt with flexibly.

In transmitting collected images, a standardized communication protocol called DICOM is generally used. A plurality of sensed images are processed in the unit of a series. A plurality of series are processed in the unit of a study. On the study unit basis, images are sequentially sensed and managed.

Figure 25:
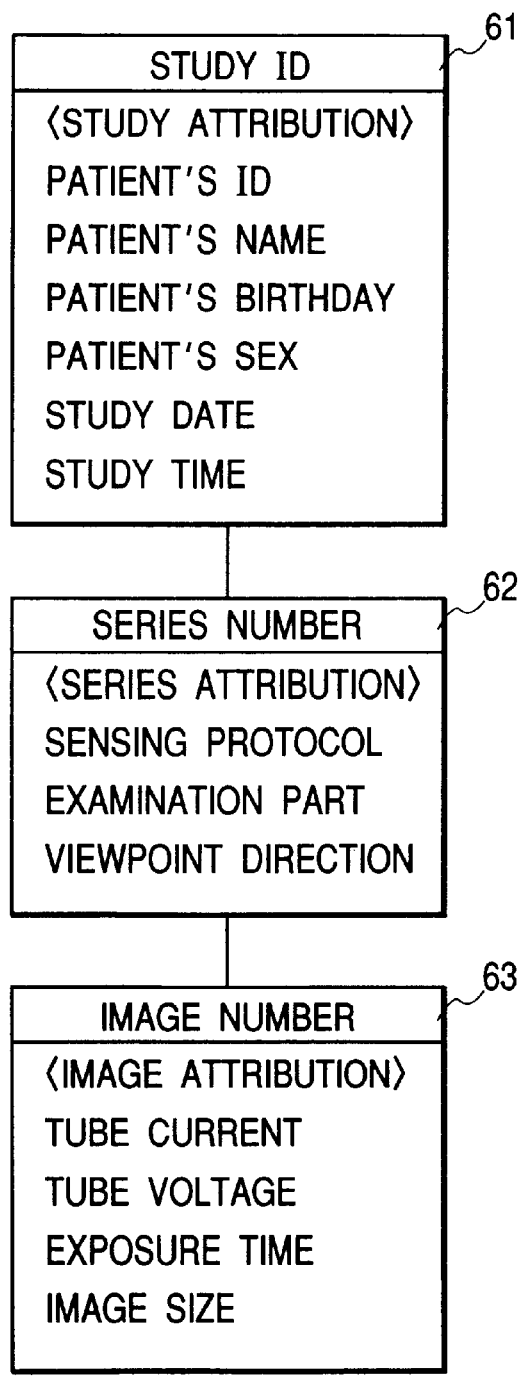
FIG. 25 is a diagram showing attributes of a study ID 61, a series number 62 and an image number 63.

FIG. 25 shows attributes of a study ID 61, a series number 62 and an image number 63. The protocol is used for examination of various modalities. The protocol is therefore dependent upon the sensing modality under the condition under which series are newly formed. In this embodiment, the digital image collection apparatus generally manages each of the images as the series.

Figure 26:
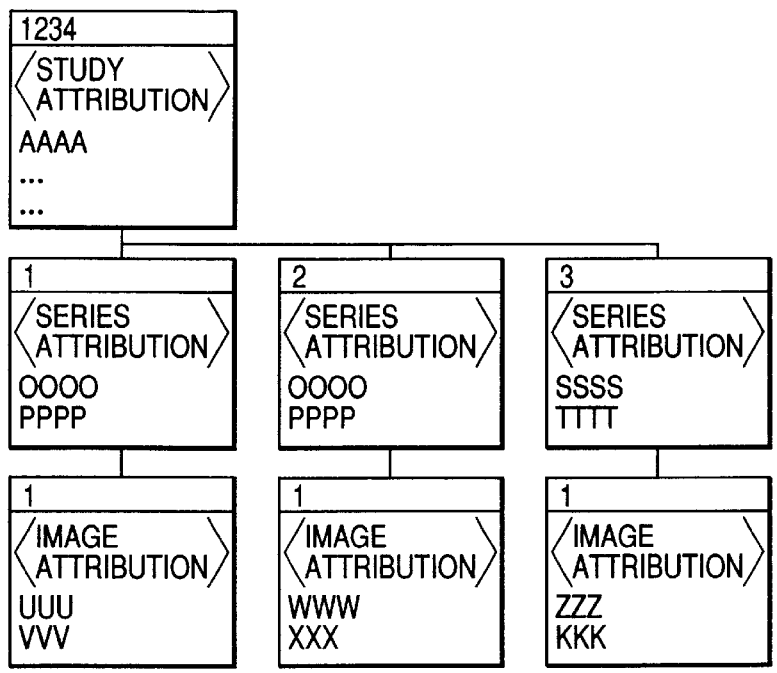
FIG. 26 shows conventional study, series and image attributes.

FIG. 26 is a diagram showing the relation between study, series and image attributes used by a conventional general digital image collection apparatus.

If there is already a series 1 and a new series 2 is to be added, a series number 2 is assigned to this new series even if the series attributes are the same. The newly generated series is added to a study 1234. With this method, a series is newly assigned to each of all sensed images when the image is formed.

Some sensing method senses several images in the same direction. For example, several images are sensed in the II-DR still image sensing. In such a case, there are several sensed images having the same series image attributes. In this case, sensed images may be added to the fixed study and series. In this embodiment, such a case can be dynamically dealt with.

This embodiment will be described with reference to FIG. 27.

Figure 27:
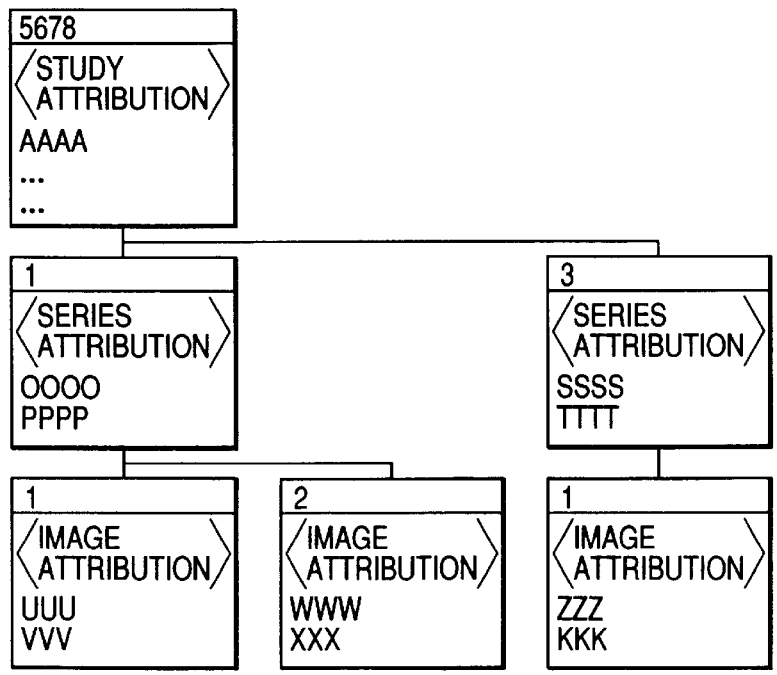
FIG. 27 is a diagram showing an example of image management according to the third embodiment of the invention.

FIG. 27 is a diagram showing an example of image management of this embodiment.

If a sensing operation is performed by using a study different from the past study with different attributes, a new study is added. In this example, the study attribute 5678 is generated. For images of this study, a new series having the series number 1 is added to the study, and sensed images are added to the series of number 1 as the image number 1. Alphanumerical values such as AAAA and 0000 shown in FIG. 27 represent attributes.

If the next sensing operation is performed under the same setting of the series attributes, i.e., under the same settings of the sensing protocol, examination part, and direction of view line, then sensed images are added to the series 1 as having the image number 2.

If the next sensing operation is performed under the setting having even one different setting in the sensing protocol, examination part and direction of view line, a series 2 is newly generated and added to the study 5678. The newly sensed image is added as having the image number 1.

One of the features of the embodiment is that if the sensing operation is performed under the attributes of the series 1 after the above-described three images were sensed, one of the following two setting modes can be selected.

Figure 28:
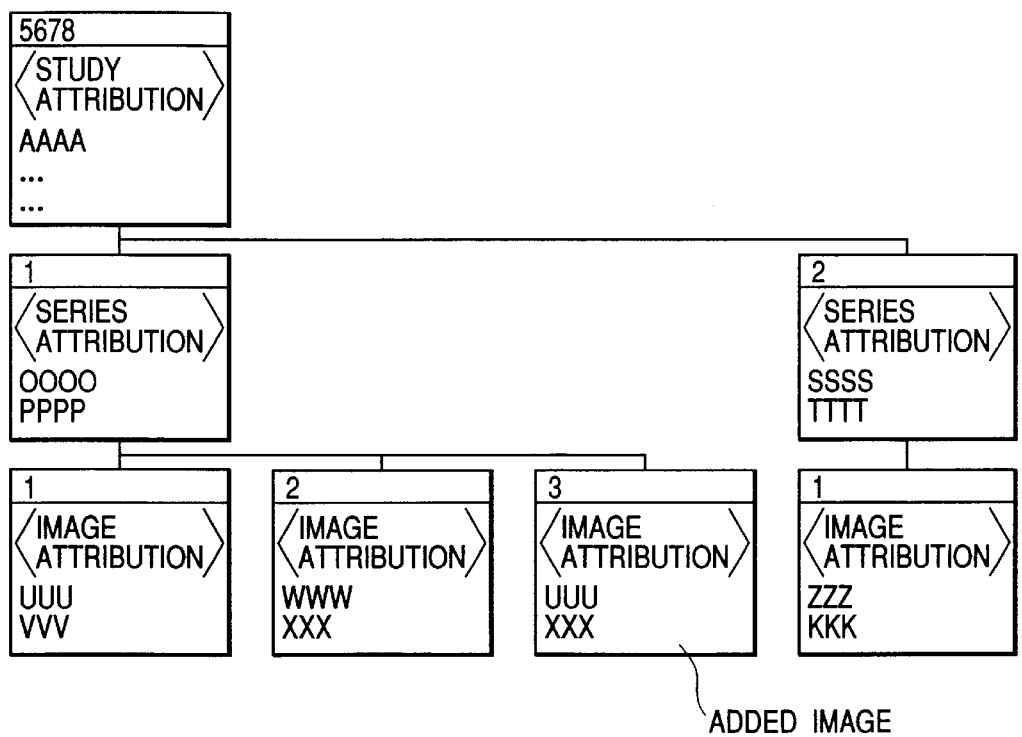
FIG. 28 is a diagram showing an example of Mode 1.

FIG. 28 is a diagram illustrating a mode 1.

In this mode, the past series having the same attributes is searched. If there is such a past series, the sensed image is added to this series. In this example, an image having the image number 3 is added to the series having the series number 1.

Figure 29:
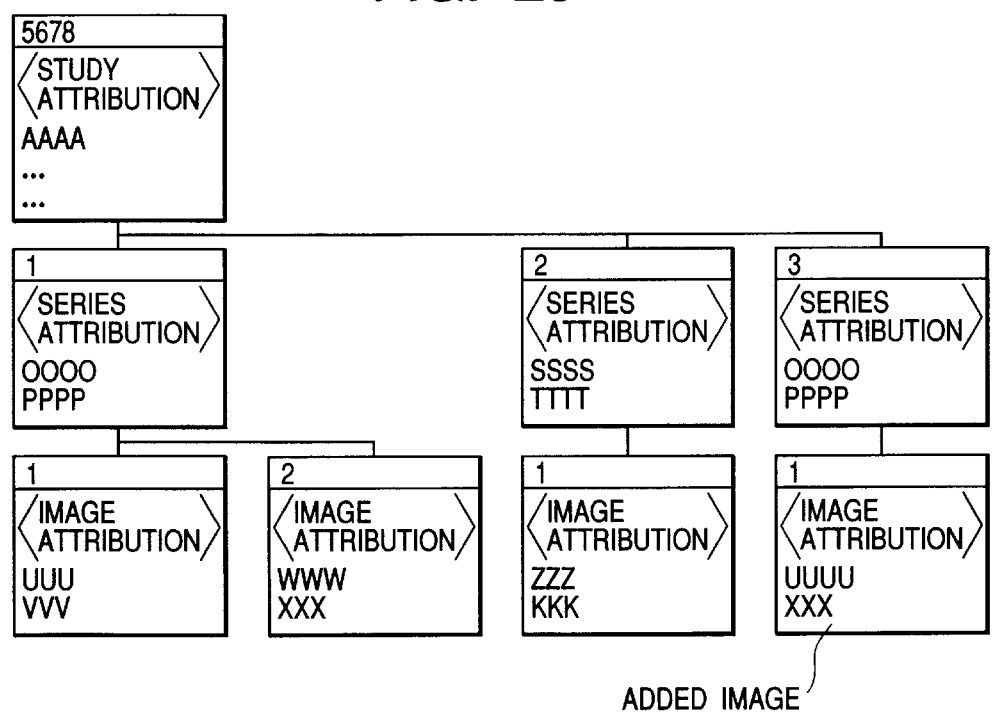
FIG. 29 is a diagram showing an example of Mode 2.

FIG. 29 is a diagram illustrating a mode 2.

In this mode, the past series having the same attributes is not searched, but the new series is generated and the sensed image is added to this series. In this example, a series having the series number 3 is generated and the image having the image number 1 is added.

With such processes, images can be managed as those images having similar attributes, so that images can be managed conveniently.

As described, according to the embodiment, patient setting, sensing condition and the like operate in cooperation with the X-ray generation apparatus control unit, solid state image pickup unit and the like, in accordance with the ordering information. Accordingly, works such as inputting sensing condition by an operator, particularly an X-ray technician, can be considerably reduced.

Next, the fourth embodiment of the invention will be described. In this embodiment, a storage medium storing program codes which realizes the functions of the first or second embodiment is supplied to an image collecting system, and a computer (or CPU, MPU) of the image collecting system reads and executes the program codes stored in the storage medium. The storage medium stores therein programs which executes the process sequences of controlling the operations of the first or second embodiment.

The storage medium may be a semiconductor memory, an optical disk, an opto-magnetic disk or a magnetic medium, for example. In addition, the storage medium may be arranged as a ROM, a RAM, a CD-ROM, a floppy disk, a magnetic tape, a magnetic card, or a non-volatile memory card, for example, which is formed by the semiconductor memory, the optical disk, the opto-magnetic disk or magnetic medium.

Figure 20:
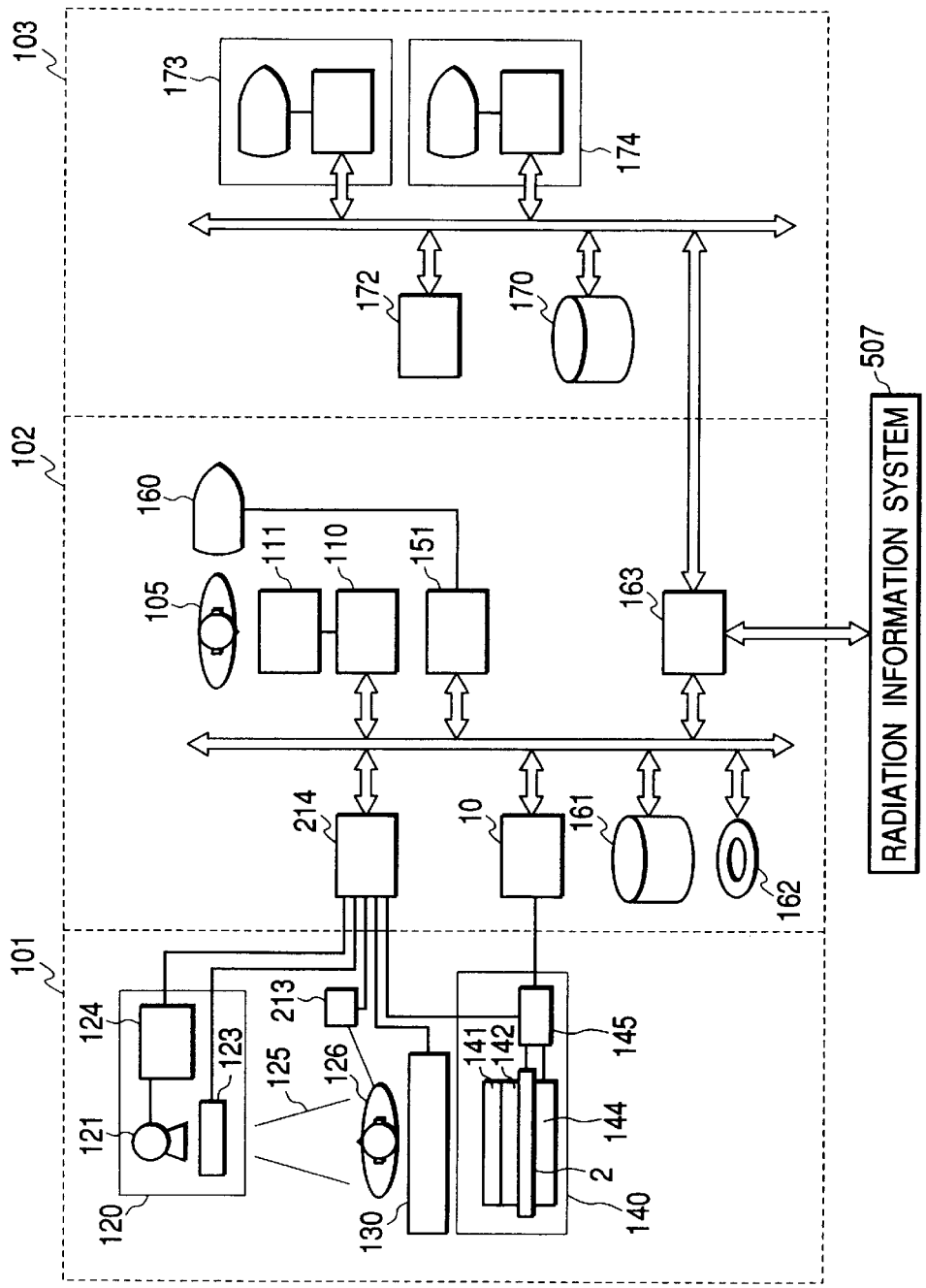
FIG. 20 is a diagram showing the structure of an X-ray image collecting system according to the second embodiment.

Therefore, other systems and apparatuses different from the systems shown in FIGS. 3, 4, and 20 may use such the storage medium, and the other system or their computers read and execute the program codes stored in the storage medium. In this manner, the same functions as those of the first and second embodiments can be realized and similar advantages can be obtained.

Furthermore, the same functions as those of the first and second embodiments can be realized and similar advantages can be obtained in the case wherein in accordance with the program codes stored in a memory of a function expansion board or unit connected to the computer supplied with the program codes, an OS or the like running on a computer or a CPU or the like of the function board or unit executes part or the whole of the actual tasks.

Many widely different embodiments of the present invention may be constructed without departing from the spirit and scope of the present invention. It should be understood that the present invention is not limited to the specific embodiments described in the specification, except as defined in the appended claims.

What is claimed is:

1. A system comprising:
   X-ray irradiating means for irradiating an X-ray;
   an image pickup unit for acquiring an image of an object by receiving the X-ray which has been irradiated onto the object and transmitted through the object;
   an input unit for inputting information
   a first control unit for changing a state of said image pickup unit between an active state and an inactive state in accordance with the information from said input unit; and
   a second control unit for determining the state of said image pickup unit on the basis of a drive notification signal from said image pickup unit, and for sending an irradiation permission signal to said X-ray irradiating means when said image pickup unit is determined to be in the active state.

2. A system according to claim 1, wherein the input information comprises information identifying an image of the object to be acquired by said image pickup unit.

3. A system according to claim 2, wherein the identifying information comprises information specifying the object.

4. A system according to claim 1, further comprising a request reception unit for receiving an image acquisition request from an external source, wherein the image acquisition request includes information specifying a kind of one or more images of the object to be acquired.

5. A system according to claim 4, wherein said input unit comprises a kind of selection unit for selecting a kind of an image to be acquired in accordance with the image acquisition request received by said reception unit.

6. A system according to claim 1, wherein said first control unit changes the state of said image pickup unit into the inactive state if image sensing by said image pickup unit is not performed for a predetermined time after the information has been input from said input unit.

7. A system according to claim 6, further comprising a display unit for displaying a notice of a lapse of the predetermined time.

8. A system according to claim 6, wherein said first control unit releases the information if image sensing by said image pickup unit is not performed for a predetermined time after the information has been input from said input unit.

9. A system according to claim 1, wherein said first control unit changes the state of said image pickup unit into the active state if the information is input from said input unit.

10. A system according to claim 9, further comprising a display unit for displaying a notice that said image pickup unit, when in the active state, is in an image acquisition-enabled state.

11. A system according to claim 4, wherein said first control unit changes the state of said image pickup unit into the inactive state if the image acquisition request for which an image acquisition is not completed is empty after an image is acquired.

12. A system according to claim 1, wherein said system is adapted to acquire an X-ray image.

13. A system according to claim 12, further comprising a condition reception unit for receiving X-ray condition information from an X-ray generation apparatus controller, wherein said first control unit changes the state of said image pickup unit into the active state in accordance with a reception of the X-ray condition information.

14. A system according to claim 12, further comprising a condition reception unit for receiving X-ray condition information from an X-ray generation apparatus controller and a setting unit for setting a grid speed parameter in accordance with the X-ray condition information.

15. A method adapted to an imaging system, the method comprising the steps of:
   inputting information from an input unit;
   changing, with a first control unit, a state of an image pickup unit between an active state and an inactive state in accordance with an input of information from the input unit;
   determining, with a second control unit, the state of the image pickup unit on the basis of a drive notification signal from the image pickup unit, and sending an irradiation permission signal to X-ray irradiation means when the image pickup unit is determined to be in the active state;

irradiating an object with an X-ray with the X-ray irradiation means when the irradiation permission signal is received by the X-ray irradiation means; and acquiring an image of the object with the image pickup unit.

16. A computer-readable storage medium storing a program code for performing a method adapted to an imaging system, the method comprising the steps of:

inputting information from an input unit;

changing, with a first control unit, a state of an image pickup unit between an active state and an inactive state in accordance with an input of information from the input unit;

determining, with a second control unit, the state of the image pickup unit on the basis of a drive notification signal from the image pickup unit, and sending an irradiation permission signal to X-ray irradiation means when the image pickup unit is determined to be in the active state;

irradiating an object with an X-ray with the X-ray irradiation means when the irradiation permission signal is received by the X-ray irradiation means; and acquiring an image of the object with the image pickup unit.

17. A system comprising:

X-ray irradiating means for irradiating an X-ray;

an image pickup unit for acquiring an image of an object by receiving the X-ray which has been irradiated onto the object and transmitted through the object;

an input unit for inputting information identifying an image of the object to be acquired by said image pickup unit;

a first control unit for changing a state of said image pickup unit between an active and an inactive state in accordance with the information from said input unit; and a second control unit for determining the state of said image pickup unit on the basis of a drive notification signal from said image pickup unit, and for sending an irradiation permission signal to said X-ray irradiating means when said image pickup unit is determined to be in the active state.

* * * * *